United States Patent
Florou et al.

(10) Patent No.: US 12,409,334 B2
(45) Date of Patent: Sep. 9, 2025

(54) MAGNETIC STIMULATION DEVICE AND METHOD

(71) Applicant: Magnetics Lab PC, Salonika (GR)

(72) Inventors: Eleftheria Florou, Salonika (GR); Nikolaos Dimitriadis, Salonika (GR)

(73) Assignee: Magnetics Lab PC, Salonika (GR)

( * ) Notice: Subject to any disclaimer, the term of this patent is extended or adjusted under 35 U.S.C. 154(b) by 0 days.

(21) Appl. No.: 18/804,175

(22) Filed: Aug. 14, 2024

(65) Prior Publication Data

US 2025/0025715 A1     Jan. 23, 2025

Related U.S. Application Data

(63) Continuation of application No. PCT/IB2023/057491, filed on Jul. 24, 2023.

(30) Foreign Application Priority Data

Jul. 17, 2023    (GR) ............................ 20230100575

(51) Int. Cl.
     *A61N 2/02*      (2006.01)
     *A61N 2/00*      (2006.01)
     *H02J 50/12*     (2016.01)

(52) U.S. Cl.
     CPC ..................................... *A61N 2/02* (2013.01)

(58) Field of Classification Search
     CPC ....................................................... A61N 2/02
     See application file for complete search history.

(56) References Cited

U.S. PATENT DOCUMENTS

| | | | |
|---|---|---|---|
| 2003/0006880 A1* | 1/2003 | Zimmer | G06K 7/0008 340/10.34 |
| 2016/0352329 A1* | 12/2016 | Southern | H05B 6/062 |
| 2021/0268300 A1* | 9/2021 | Peled | A61N 2/02 |

FOREIGN PATENT DOCUMENTS

| | | | |
|---|---|---|---|
| WO | 2023/280332 | 1/2023 | |
| WO | WO-2023280322 A1 * | 1/2023 | A61M 39/06 |

OTHER PUBLICATIONS

International Search Report and Written Opinion based on co-pending PCT International Application No. PCT/IB2023/057491, dated Apr. 16, 2024; pp. 1-12.

(Continued)

*Primary Examiner* — Carrie R Dorna
*Assistant Examiner* — Joshua Daryl D Lannu
(74) *Attorney, Agent, or Firm* — McCarter & English, LLC

(57) ABSTRACT

The present invention concerns a novel magnetic stimulation device and method with optimized energy usage and improved performance comprising: a magnetic field generating device, a first energy storage device and a second energy storage device connected in series to form an electrical oscillating resonant circuit; an energy source coupled to the first energy storage device; and a switch to allow charging of the first energy storage device from the energy source and initiating electrical oscillation of the resonant circuit, wherein after the initiation of the electrical oscillation the two energy storage devices repetitively exchange electric charge through the magnetic field generating device due to the electrical oscillation of the resonant circuit and a time varying magnetic field is generated. The time varying magnetic field induces electric currents in biological tissues that stimulate them.

18 Claims, 25 Drawing Sheets

(56) References Cited

OTHER PUBLICATIONS

International Search Report based on PCT International Application No. PCT/IB2023/057491, dated Apr. 16, 2024, 4 Pages.
Written Opinion based on PCT International Application No. PCT/IB2023/057491, dated Apr. 16, 2024, 7 Pages.

* cited by examiner

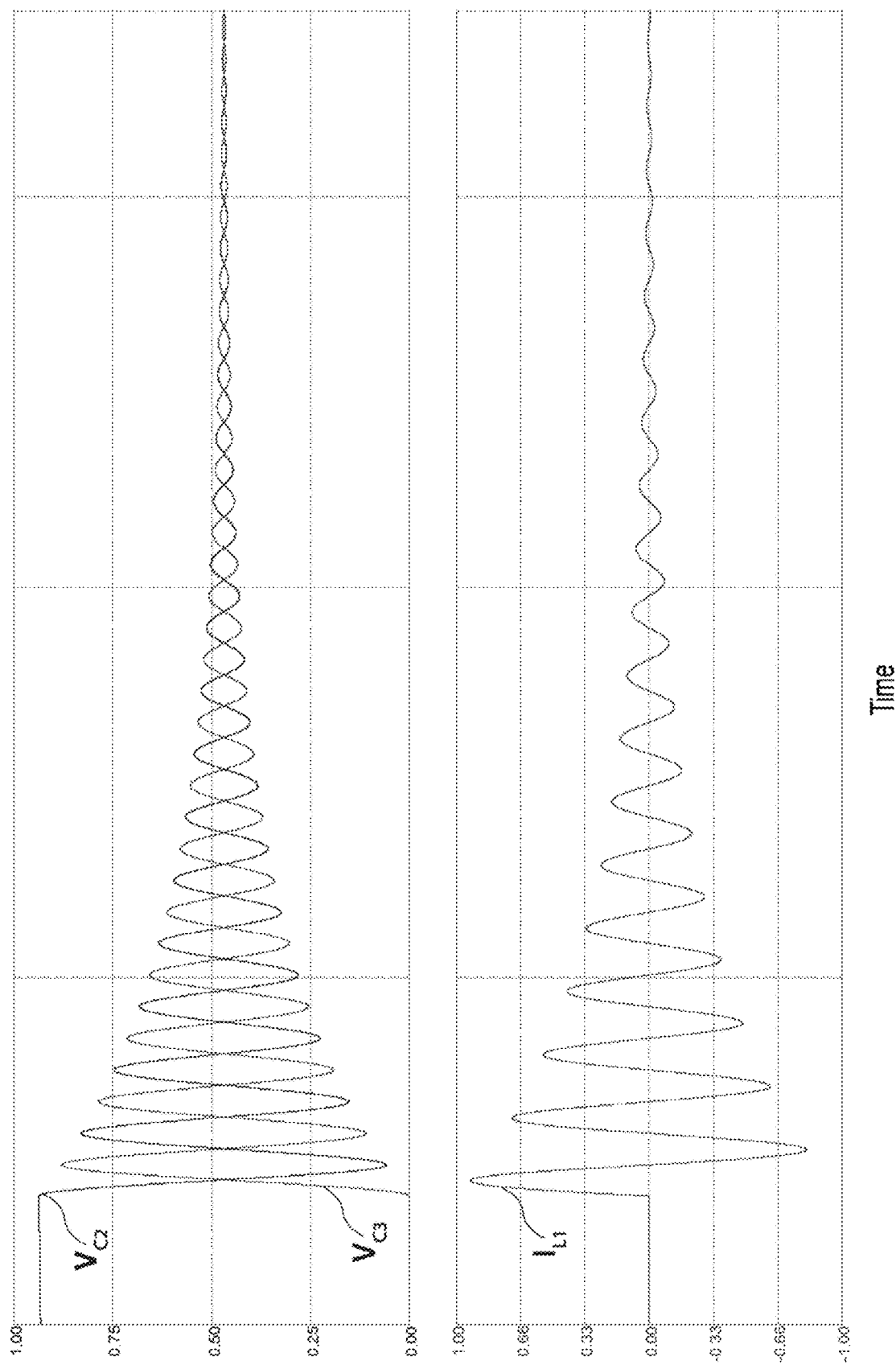

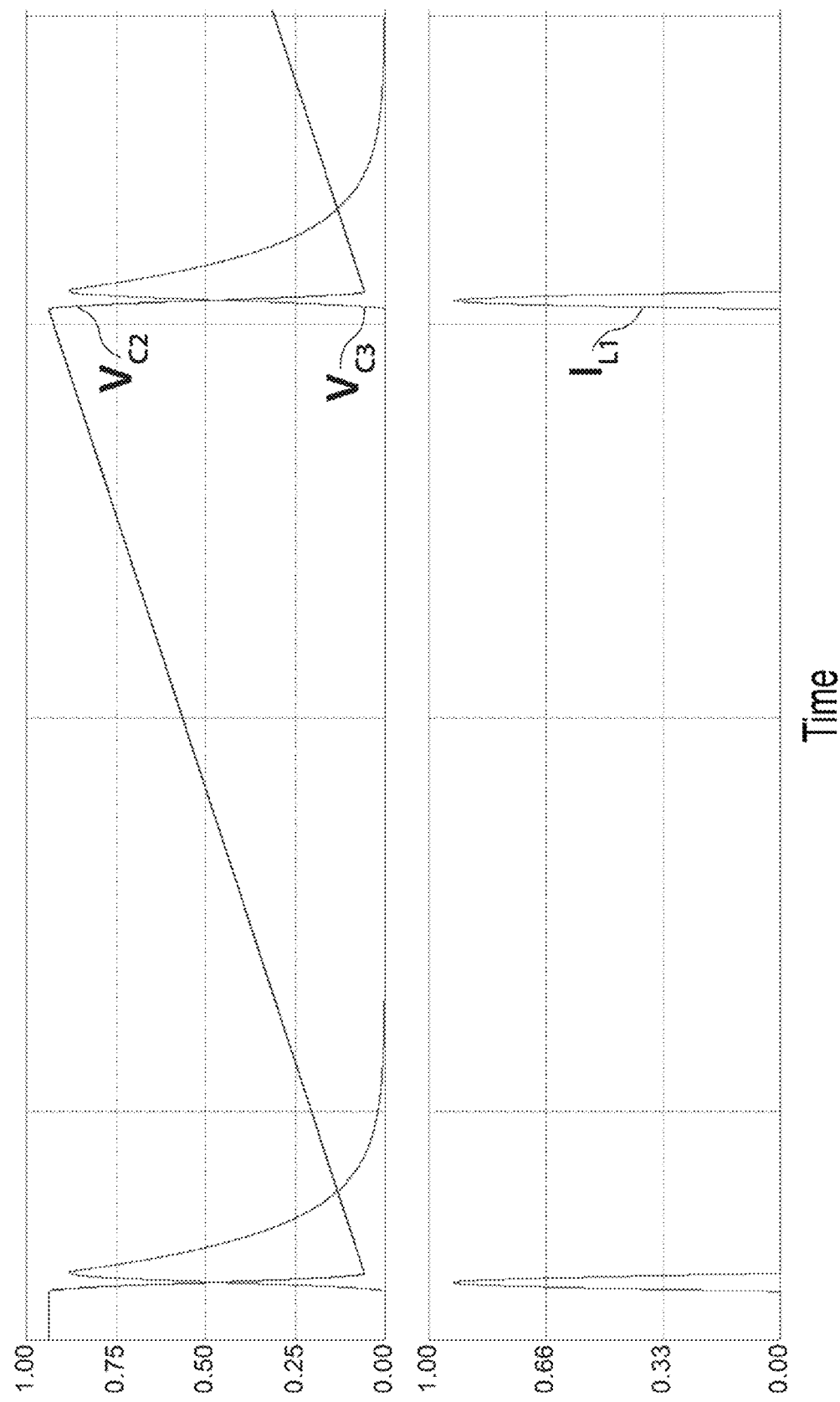

MAGNETIC STIMULATION DEVICE AND METHOD

CROSS-REFERENCE TO RELATED APPLICATIONS

This application is a continuation of PCT Application No. PCT/IB2023/057491, filed Jul. 24, 2023, which claims the benefit of Greek patent application No. 20230100575, filed Jul. 17, 2023, each of which is incorporated herein, in its entirety, by reference.

FIELD

The present invention relates to a device and method for generating magnetic stimulation for stimulating biological tissues.

BACKGROUND

Magnetic stimulation is a method used for stimulating cells by applying an external time varying magnetic field which induces electric currents in the intracellular and extracellular space that cause the cell membranes to become depolarized and trigger action potentials. The external time varying magnetic field can excite different types of cells that include nerve cells of the central and peripheral nervous system and muscle cells. The effects on the physiology and the biological reactions diversify according to the magnetic field characteristics thus allowing a broad range of applications for medical and research purposes in humans and animals. The method is non-invasive, contactless, sterile, can be painless and suitable for stimulating deeper lying tissue structures as the tissue is permeable to the magnetic field. Because of the above important advantages, the magnetic stimulation has evolved to a valuable tool used for therapeutic and research purposes which is widely used in various clinical and scientific fields.

The time varying magnetic field is produced by a device where existing magnetic stimulation devices include in their basic configuration an electric energy source, a capacitor that is charged from the energy source, a coil and a switch that allows the charging of the capacitor from the energy source and the discharging of the capacitor through the coil in the form of high amplitude and short duration current pulses. The time varying magnetic field is generated from the coil when the current pulses pass through it and can reach a peak value of magnetic flux density of several Tesla. Due to the short duration of the current pulses, the current can reach an instant value of several thousand Amperes. A way of categorizing the magnetic stimulation devices is by the waveform of the current pulses that flow through the coil which depicts the change of the amplitude of the current with time, most common types being the polyphasic pulse which consists of positive and negative half-periods of a multiple-cycle damped sinusoid, the monophasic pulse which consists of a positive rapid rise from zero to peak value and then a slow decay back to zero, the biphasic pulse which consists of a positive and a negative half-period of a one-cycle damped sinusoid, the half-sine pulse which consists of a positive half period of a sinusoid and the paired- or dual-pulse which consist of two polyphasic or two monophasic or two biphasic or two half-sine pulses separated by a selectable time interval and with independently selectable amplitudes. Another critical aspect of the performance of the magnetic stimulation devices is the voltage drop of the capacitor between the start and the end of each pulse attributed to losses because of ohmic resistance. A higher voltage drop leads to a lower voltage at the start of the next pulse if the voltage drop is not replenished, which results in a current pulse of decreased amplitude and decreased rate of change thus to weaker stimulation. If the voltage drop is replenished from the energy source in order for the next pulse to be the same as the previous one, then the higher the voltage drop the more time the energy source requires to replenish it due to the fact that the electric energy source charges the capacitor with a certain rate based on its current output and the required time to replenish it is a limiting factor of the minimum time interval between consecutive pulses of the same amplitude or, if expressed in the frequency domain, of the maximum pulse repetition rate of a magnetic stimulation device. The voltage drop if normalized to the operating voltage and expressed as a % percent is an inherent characteristic of a magnetic stimulation device. Existing devices incorporate therefore recovery circuits that allow part of the initial voltage of the capacitor to be recovered in order for the voltage drop to be limited. Consequently and taking into consideration that the contribution of the stimulation of the tissues to the voltage drop is a very small fraction as the absorbed energy required for stimulation is a minor fraction of the total pulse energy, the optimization of the design of a magnetic stimulator requires the least possible losses due to ohmic resistance and the highest possible voltage recovery.

Existing devices and methods provide limited efficiency and performance. These limitations are posed when reverse voltage is applied to the output of the energy source which requires the use of protective circuits that result in increased losses due to additional ohmic resistance and higher rating components inside the energy source that lead also in higher switching and conducting losses. Another disadvantage is the case of reverse charging the capacitor that increases its voltage rating, its size and cost. Additionally, reverse charging the capacitor leads to almost doubling the working peak to peak voltage of the device, creating less safe devices and the need for additional electrical safety measures. On another aspect, devices that include the stimulation coil within the capacitor's charging circuit, so that current flows through the stimulation coil during capacitor's charging phase, are restricted by the additional losses due to ohmic resistance of the coil during the capacitor's charging phase, produce unnecessary additional coil heating and greater demand for coil cooling, the need for reduced but still existing protective circuits for the energy source is created and a magnetic field with uncommon characteristics and non-investigated effects in the field of magnetic stimulation of tissues is emitted during charging. In other cases, designs of devices include voltage recovery methods to increase efficiency but that is accomplished to a limited only extent, at the expense of increased complexity and cost and because additional operating switches are required that subsequently import additional losses because of ohmic resistance. Operating switches and protective circuits with typical ratings for a magnetic stimulator import ohmic resistance in the range of tens of milliohms that contributes to the % Voltage Drop more than other components, like the connecting cables, of a magnetic stimulator. Present devices use a variety of different shape, size and orientation coils where coil heating is produced due to the high currents. To satisfy the requirement of providing different pulse shapes and stimulation patterns, devices incorporate circuit designs of increased complexity accompanied by higher losses because of higher ohmic resistance and increased synchronization requirements for the operation of the different components.

Based on the analysis of the prior art, there is a need for improved magnetic stimulation devices and methods that are not limited by the disadvantages of the existing technology.

SUMMARY

The present invention concerns a novel magnetic stimulation device and method with optimized energy usage and improved performance comprising: a magnetic field generating device, a first energy storage device and a second energy storage device connected in series to form an electrical oscillating resonant circuit; an energy source coupled to the first energy storage device; and a switch to allow charging of the first energy storage device from the energy source and initiating electrical oscillation of the resonant circuit, wherein after the initiation of the electrical oscillation the two energy storage devices repetitively exchange electric charge through the magnetic field generating device due to the electrical oscillation of the resonant circuit and a time varying magnetic field is generated. This circuit can be described as the basic circuit of the invention. The time varying magnetic field induces electric currents in biological tissues that stimulates them. When the switch is open, the energy source charges the first energy storage device and as soon as the switch is closed electrical oscillation of the resonant circuit initiates. Reverse voltage is not applied to the output of the energy source at any time and the two energy storage devices are never reversely charged.

The voltage across the terminals of each of the two energy storage devices has always the same polarity.

No current is flowing through the magnetic field generating device during charging of the first energy storage device from the energy source.

The energy source is protected against reverse voltage polarity without the use of electrical protective means.

After the initiation of the electrical oscillation of the resonant circuit the two energy storage devices repetitively exchange electric charge without the operation of any switch.

Furthermore, the first energy storage device is coupled to the energy source with the minimum possible length of conductors and without any electrical protective means between them, thus contributing to minimizing losses during charging and making the device safer. During electrical oscillation, electric charge is repetitively exchanged between the two energy storage devices through the magnetic field generating device without requiring the operation of any switch that would increase complexity and losses due to ohmic resistance, providing a highly efficient voltage recovery.

In the present invention, by adding to the switch of the basic circuit the functionality to open and close at selectable time points in order to halt the electrical oscillation of the resonant circuit, the resonant circuit can generate different waveforms of current pulses, with a low % Voltage Drop and up to high pulse repetition rates due to the highly efficient voltage recovery and the minimum losses of the minimized ohmic resistance because of the simplicity of the circuit.

The present invention, by adapting the position of the switch of the basic circuit to allow charging of the second energy storage device from the energy source, instead of the first energy storage device, and initiating electrical oscillation of the resonant circuit, provides the disadvantage of current flowing through the magnetic field generating device during charging of the second energy storage device from the energy source and the advantage of requiring fewer switches to be added to this implementation compared to the basic circuit for the generation of paired- or dual-pulses. In other words, in the present invention, the position of the switch is adapted to allow charging of the second energy storage device from the energy source and initiating electrical oscillation of the resonant circuit.

The present invention, further enhances the performance by adding to the basic circuit with the added switch functionality a serial connection of a resistor and a second switch and the serial connection of the resistor and the second switch is connected in parallel to the second energy storage device to selectively discharge either one of the two or both the energy storage devices and provides the highest efficiency and performance for the generation of polyphasic and biphasic current pulses.

The present invention, by further adding to the basic circuit with the added switch functionality and the added selective discharging functionality a serial connection of a third switch and a second resistor and the serial connection of the third switch and the second resistor is connected in parallel to the serial connection of the first switch and the magnetic field generating device, provides the highest efficiency and performance for the generation of monophasic current pulses.

The present invention, by further adding to the basic circuit with the added switch functionality and the added selective discharging functionality a serial connection of a third switch and a second magnetic field generating device and the serial connection of the third switch and the second magnetic field generating device is connected in parallel to the serial connection of the first switch and the first magnetic field generating device, provides the highest efficiency and performance for the generation of half-sine current pulses.

The present invention, by further adding to the basic circuit with the added switch functionality and the added selective discharging functionality a serial connection of a third switch and a second resistor and a serial connection of a fourth switch and a second magnetic field generating device, wherein the serial connection of the third switch and the second resistor and the serial connection of the fourth switch and the second magnetic field generating device are connected in parallel to the serial connection of the first switch and the first magnetic field generating device, provides the highest efficiency and performance for the generation of polyphasic, biphasic, monophasic and half-sine current pulses and any combination of them by requiring a minimum number of four switches and a minimum complexity with minimized losses due to ohmic resistance and minimized synchronization requirements.

The present invention, by further adding to the basic circuit with the added switch functionality and the added selective discharging functionality a serial connection of a third energy storage device and a third switch and the serial connection of the third energy storage device and the third switch is connected in parallel to the serial connection of the magnetic field generating device and the second energy storage device, wherein the third energy storage device is further coupled to the energy source; and a fourth and a fifth switch to allow the energy source to selectively charge either only the first energy storage device or only the third energy storage device or both, provides the possibility to produce pairs of current pulses of the same or different type, or single-pulses of higher amplitude of any type. The amplitude of each of the current pulse of a pair can be adjusted independently via the fourth and the fifth switch and also the time interval between the current pulses of a pair can be adjusted independently to any value via the first and the third switch. A single-pulse of higher amplitude is a pulse of higher amplitude due to the combination of the first energy storage device with the third energy storage device.

The present invention can further reduce losses due to ohmic resistance by disposing the energy storage devices within one casing because of shortening the length of the connecting conductors of the circuit.

According to the present invention, each energy storage device can comprise at least one capacitor with the capacitances of the energy storage devices are preferably equal because for equal capacitances the energy transfer and the voltage recovery between the energy storage devices during oscillation are maximized.

The present invention, by implementing independently selectable capacitance of each energy storage device provides the possibility to selectively adjust the duration of the current pulses in the case the capacitances of the energy storage devices are changed and after the change being equal and the possibility to selectively adjust the voltage transfer ratio between the energy storage devices during oscillation in the case the capacitances of the energy storage devices are changed and after the change not being equal.

The present invention, by further adding to the basic circuit a plurality of switches and magnetic field generating devices, wherein each switch is connected in series with one magnetic field generating device forming a serial connection and all serial connections are connected in parallel to one another and in parallel to the serial connection of the first switch and the first magnetic field generating device, provides the possibility to selectively engage similar or different, simultaneously or not, magnetic field generating devices in the basic resonant circuit which facilitates the application of magnetic stimulation in larger or different areas, in shorter times, with magnetic field generating devices of different shape, size, orientation and focus or with more complex orientations and focuses when simultaneously applying more than one magnetic field generating devices at an area.

The present invention, by further adding to the basic circuit a plurality of electrical oscillating resonant circuits each constituted by a connection in series of two energy storage devices, a switch and a magnetic field generating device, wherein one of the two energy storage devices of each electrical oscillating resonant circuit is coupled with a switch to the energy source and to the other electrical oscillating resonant circuits, provides the possibility of selectively generating independently to one another time-varying magnetic fields either simultaneously or not.

The present invention, by further adding a control unit to control the energy source and the switches provides the possibility for continuous adjustment and modulation of the output of the energy source, of the amplitude of the current pulses, of the repetition rate of the current pulses and of the type of the current pulses, wherein the current pulses include the current pulses flowing through the magnetic field generating devices.

The present invention is used to biological tissues, wherein time varying field induce electric currents in biological tissues.

According to the present invention, a method is provided of generating magnetic stimulation in tissues, the method comprising: providing an energy source; charging an energy storage device connected in series to a magnetic field generating device and to another energy storage device that form an electrical oscillating resonant circuit; and allowing electrical oscillation of the resonant circuit that generates electric current flowing through the magnetic field generating device that produce a time varying magnetic field which induces electric currents in tissues.

According to another aspect of the method of the current invention, the method comprises of the following steps: providing an energy source; charging an energy storage device connected in series to a magnetic field generating device that form an electrical oscillating resonant circuit; connecting a second energy storage device in series to the serial connection of the first energy storage device and the magnetic field generating device that form a new electrical oscillating resonant circuit; and allowing electrical oscillation of the new resonant circuit that generates electric current flowing through the magnetic field generating device that produce a time varying magnetic field which induces electric currents in tissues.

BRIEF DESCRIPTION OF THE DRAWINGS

FIGS. 2A to 2C are illustrative graphs of the voltages of the two energy storage devices and the current of the magnetic field generating device generated by using the embodiment of FIG. 1, showing a polyphasic, a biphasic and a half-sine pulse respectively.

FIGS. 6A to 6D are illustrative graphs of the voltages of the two energy storage devices and the current of the magnetic field generating device generated by using the embodiment of FIG. 5, showing two polyphasic, two biphasic, two half-sine and two monophasic pulses respectively.

DETAILED DESCRIPTION

Figure 1:
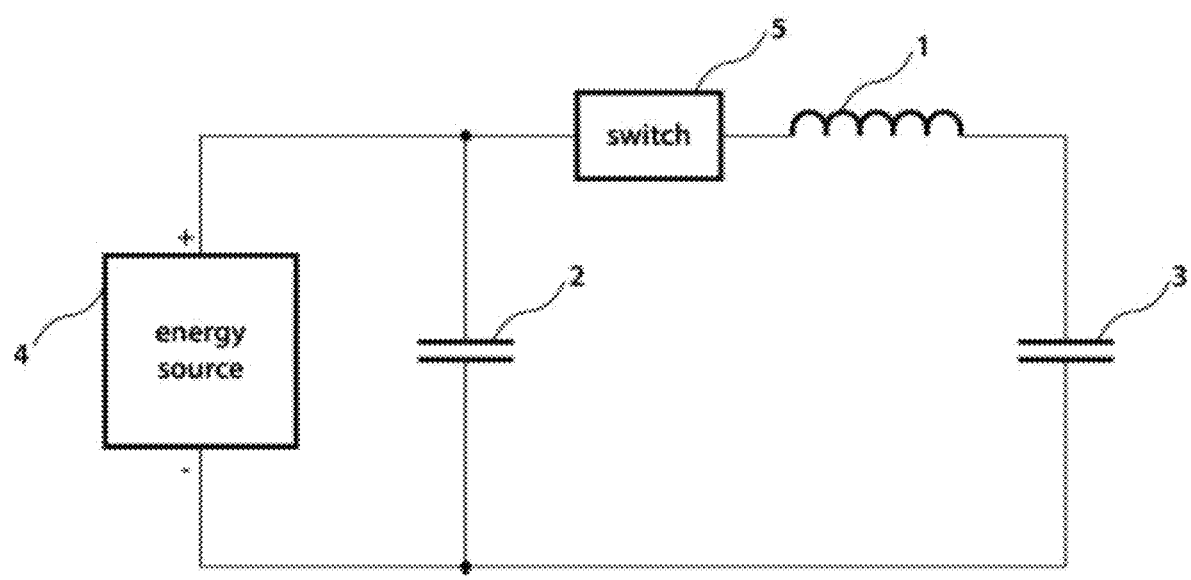
FIG. 1 is an illustrative diagram of an embodiment of a magnetic stimulator comprising a magnetic field generating device, a first energy storage device and a second energy storage device connected in series, where the capacitances of the two energy storage devices are equal, an energy source connected in parallel to the first energy storage device and a switch connected in series between the first energy storage device and the magnetic field generating device and included in the same branch of the circuit with the magnetic field generating device.

The present invention is based on the unique inventive concept of a magnetic stimulator with an electrical resonant circuit that is constituted by the in series connection of two energy storage devices and a magnetic field generating device. As a resonant circuit the electric field energy stored in the one energy storage device is transferred to the other energy storage device with the contribution of the magnetic field generating device due to its inductance. In order for the oscillation to initiate the necessary and sufficient condition is a voltage difference to exist between the two energy storage devices. This is a differentiation between the resonant circuit of the present invention and all RLC resonant circuits of other magnetic stimulators that incorporate only one energy storage device in their resonant circuit. The resonant circuit of the present invention oscillates when a voltage difference exists between the two energy storage devices and stops to oscillate when the voltages of the two energy storage devices are equalized while the current of the magnetic field generating device is zero. The current, which always flow through the magnetic field generating device, has a direction that is inverted from half-period to half-period. The resonant circuits that incorporate only one energy storage device oscillate when a voltage other than zero is present on their only one energy storage device and seize to oscillate when the voltage on their only one energy storage device is equal to zero while the current of the magnetic field generating device is zero. A unique attribute of the resonant circuit of the present inversion is that the voltage polarity on each energy storage device remains always the same and never inverts. An additional unique attribute of the resonant circuit of the present inversion is that the current which the energy source outputs for charging does not need to flow through the magnetic field generating device. Most of the equations and functions that describe the underdamped response of an RLC resonant circuit apply as well to the resonant circuit of the present invention with the alterations of the voltage $V_C$ of a capacitor of a typical RLC circuit being replaced by the $\Delta V_C = V_{C2} - V_{C3}$ voltage difference of the two energy storage devices $C_2$ and $C_3$ of the resonant circuit of the present invention and the capacitance C of a capacitor of a typical RLC circuit being replaced by the overall capacitance of the two energy storage devices $C_2$ and $C_3$ connected in series in the resonant circuit of the present invention:

$$C_{2+3 \, in \, series} = \frac{1}{\frac{1}{C_2} + \frac{1}{C_3}}$$

R still represents the total resistance of the circuit which is the sum of ohmic resistances of the switching devices, of the magnetic field generating device and of the connecting cables of the circuit.

The unique inventive concept of the invention provides a method for generating magnetic stimulation in tissues by charging an energy storage device with an energy source, by having another energy storage device and a magnetic field generating device where the two energy storage devices and the magnetic field generating device are connected in series and constitute an electrical oscillating resonant circuit and by allowing the electrical oscillation of the resonant circuit, due to the voltage difference between the two energy storage devices, electric current flows from the one energy storage device to the other and back with the contribution of the magnetic field generating device around of which a time-varying magnetic field is generated. On another aspect, the present invention's method can be utilized in an existing RLC resonant circuit where a second energy storage device can be added to the existing RLC resonant circuit by connecting it in series to the existing energy storage device and magnetic field generating device, to form a new resonant circuit under the unique inventive concept of the current invention, so that instead of charging and discharging the one energy storage device of the existing RLC resonant circuit with the contribution of the magnetic field generating device, to have the charge exchanged between the two energy storage devices with the contribution of the magnetic field generating device.

DESCRIPTION OF EMBODIMENTS

Referring to FIG. 1, an illustrative diagram of an embodiment of a magnetic stimulator for producing polyphasic, biphasic and half-sine types of current pulses is shown. The embodiment of FIG. 1 comprises of a magnetic field generating device (1), a first energy storage device (2) and a second energy storage device (3) connected in series to form an electrical oscillating resonant circuit; an energy source (4) coupled to the first energy storage device (2); and a switch (5) to allow charging of the first energy storage device (2) from the energy source (4) and initiating electrical oscillation of the resonant circuit, wherein after the initiation of the electrical oscillation the two energy storage devices (2) and (3) repetitively exchange electric charge through the magnetic field generating device (1) due to the electrical oscillation of the resonant circuit and a time varying magnetic field is generated. More specifically the resonant circuit of the embodiment of FIG. 1 comprises the connection in series of the first energy storage device (2) with a capacitance $C_2$, the second energy storage device (3) with a capacitance Cs where, by way of example, the capacitance Cs is equal to the capacitance $C_2$ and the magnetic field generating device (1) with an inductance $L_1$. One example of energy storage device is a capacitor. An example of magnetic field generating device is a coil. The energy source (4) is connected in parallel to the first energy storage device (2). A switch (5) is connected in series between the first energy storage device (2) and the magnetic field generating device (1) and included in the same branch of the circuit with the magnetic field generating device (1). The switch (5) can be implemented with any kind of switching components or their combinations, such as thyristor, diode, IGBT, MOSFET, JFET, BJT. Other switching components may be used, consistent with the spirit of the invention. The above embodiment contains the minimum parts, in order for the invention to be functional. Other well known materials which are commonly used in magnetic stimulators may be added in any embodiment of the present invention, but are not essential, neither are associated with the subject-matter of the present invention, nor they modify it in some way. Indicatively, apart from the coil which is contained inside a coil casing that is flexible adjusted to the enclosure, as complementary parts may be a multi-joint support arm for the coil casing, a coil cooling system by means of airflow or fluid media or other cooling technologies and interchangeable coils of different shape, size and orientation each enclosed in its own casing. Equivalent alternative embodiment of the embodiment shown in FIG. 1 with the same features, operation and performance occurs when the positions of the switch (5) and the magnetic field generating device (1) are mutually exchanged. The possibility of the embodiment of FIG. 1 to generate different types of current pulses is not restricted to the commonly used types but is extended to the generation of any arbitrary waveform of current pulse which can be generated by accordingly adjusting the selected time points of opening and closing the switch (5). Initially the switch (5) is open and the energy source (4) starts to charge the first energy storage device (2) up to a selectable voltage value $V_{C2}$. The second energy storage device (3) is not charged $V_{C3}$=0V and its voltage remains zero during the charging phase of the first energy storage device (2) due to the open switch (5). After the selected $V_{C2}$ is reached, the switch (5) closes and the voltage difference between the two energy storage devices imposes the initiation of the oscillation that drives a current from the first energy storage device (2) to the second energy storage device (3) through the magnetic field generating device (1). During the first T/4 the current is increased until it reaches its peak positive value and a time varying magnetic field is generated around the magnetic field generating device (1) until the voltages of the two energy storage devices become equal with a value of $V_{C2}/2$. In the second T/4 the decreasing with time magnetic field induces an electromotive force according to Faraday's law:

$$\nabla \times \vec{E} = -\frac{\partial \vec{B}}{\partial t}$$

that drives the current to continue to flow from its peak positive value to zero until the end of the first half-period. Due to losses attributed to ohmic resistance, at the end of the first half-period, the second energy storage device (3) is charged with a voltage $V_{C2}$ minus a minimum voltage decrement and the first energy storage device (2) is not fully discharged but retains a minimum voltage increment over zero. Because of this new voltage difference, the two energy storage devices begin again to exchange charge during the second half-period in a similar manner to the first half-period during which the current flows in the opposite direction. At the end of the third T/4 the voltages of the two energy storage devices are again equalized. At the end of the second half-period, the two energy storage devices are charged with almost their initial voltages, $V_{C2}$ minus a minimum voltage decrement the first energy storage device (2) and with a minimum voltage increment over zero the second energy storage device (3) because of the ohmic resistance losses.

Figure 2B:
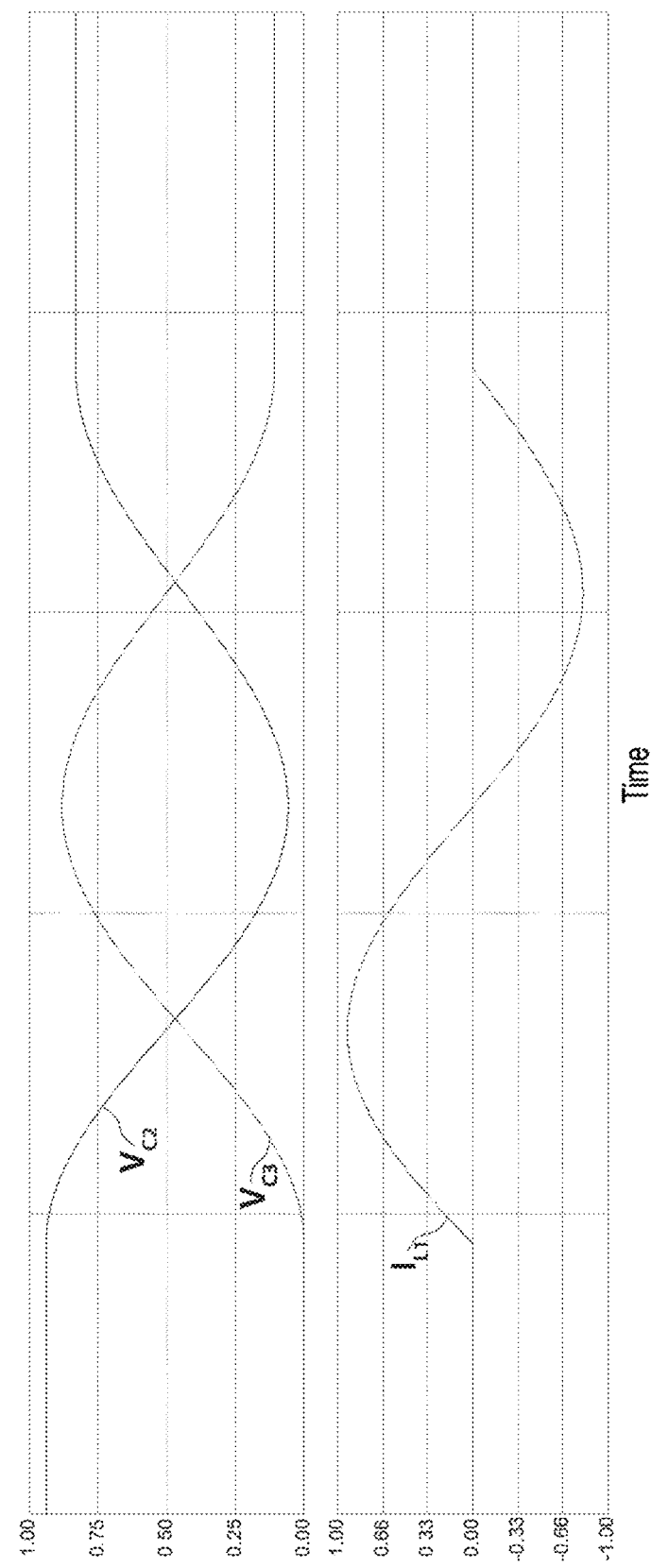

The waveforms of the voltages of the two energy storage devices (2) and (3) and the waveform of the current flowing through the magnetic field generating device (1) during a full period are depicted in FIG. 2B. The pulse of current consists of a positive and a negative half-period, it reaches a high amplitude of the order of thousands amperes, has a short period of the order of hundreds microseconds and its shape is described as a one-cycle damped sinusoid. The current $I_{L1}(t)$ is defined as the current flowing through the magnetic field generating device (1) and is obtained from the function:

$$I_{L1}(t) = \frac{\Delta V_c}{L\omega_d} e^{-at} \sin\omega_d t$$

where $\Delta V_C = V_{C2} - V_{C3}$, $a = R/2L$, $\omega_d^2 = (LC)^{-1} - a^2$. R, L and C are the total ohmic resistance, total inductance and total capacitance of the circuit, respectively. The total ohmic resistance of the circuit is the sum of ohmic resistances of the switching devices, of the magnetic field generating device and of the connecting cables of the circuit. The total inductance of the circuit is regarded equal to $L_1$ as the parasitic inductance is negligible:

$$L \approx L_1$$

The total capacitance of the circuit is regarded equal to $C_{2+3}$ in series as the parasitic capacitance is negligible:

$$C \approx C_{2+3\,in\,series}$$

The period for the underdamped natural oscillation of the circuit is:

$$T_d = \frac{1}{f_d}$$

where $$f_d = \frac{\omega_d}{2\pi}, \omega_d = \omega_n\sqrt{1-\zeta^2}, \omega_n = \frac{1}{\sqrt{L_1 C_{2+3\,in\,series}}}, \zeta = \frac{R}{2}\sqrt{\frac{C_{2+3\,in\,series}}{L_1}}.$$

The magnetic field generating device (1), which is an integral part of the resonant circuit, is also the stimulation mean that is placed over the stimulating area of the tissues. The magnetic flux density B (t) of the generated time varying magnetic field around the magnetic field generating device (1) is dependent on the current $I_{L1}(t)$ that flows through the magnetic field generating device (1) according to Ampere's law:

$$\nabla \times \vec{H} = \vec{J}$$

The magnetic field B (t) penetrates through the tissues and induces an electric field E which is proportional to the rate of change of B (t) based on Faraday's law. The induced E cause a flow of current in the tissues since they are electrically conductible and this flow of current generates the depolarization of the cell membranes and the trigger of action potentials. The above analysis leads to the conclusion that the effect on the cell membrane potential is proportional to the rate of change of the current $I_{L1}(t)$ that flows through the magnetic field generating device (1). Based on the facts that for all RLC resonant circuits and also for the resonant circuit of the present invention the values of R, L and C are regarded fixed without fluctuating and the period computed with these values is regarded also fixed, consequently is deduced that in order to increase the $I_{L1max}$ and the $(dI_{L1}/dt)_{max}$ one must increase the multiplier $V_C$ for a typical RLC resonant circuit or the multiplier $\Delta V_C$ for the resonant circuit of the present invention, as revealed from the $I_{L1}(t)$ function. Furthermore, since magnetic stimulators operate with stimulation protocols that require continuous emission of several thousands successive pulses and is beneficial to conclude the stimulation protocols in the shortest possible time or operate with stimulation protocols that require high pulse repetition rates in order to invoke different physiological reactions, it becomes decisive for their performance to be able to emit pulses with the highest possible pulse repetition rate which is dictated by how fast the circuit is able from the end of one pulse to charge again the one energy storage device to the $V_C$ voltage for a typical RLC resonant circuit or the two energy storage devices to the $\Delta V_C$ voltage difference for the resonant circuit of the present invention, for the next pulse to follow. Between the start of a pulse and the end of the same pulse, both for typical RLC resonant circuits and for the resonant circuit of the present invention, a drop in the voltage $V_C$ or a drop in the voltage difference $\Delta V_C$ respectively is unavoidable due to the damped response. But it is an inherent characteristic of each circuit how successfully it is able to recover part of the $V_C$ or part of the $\Delta V_C$ at the end of each pulse emitted. Therefore in an objective manner the efficiency and performance of a resonant circuit can be described by the % Voltage Drop, defined as:

$$\% \text{ Voltage Drop} = \frac{V_{c,start\,of\,pulse} - V_{c,end\,of\,pulse}}{V_{c,start\,of\,pulse}} \times 100$$

for typical RLC resonant circuits $$\% \text{ Voltage Drop} = \frac{\Delta V_{c,start\,of\,pulse} - \Delta V_{c,end\,of\,pulse}}{\Delta V_{c,start\,of\,pulse}} \times 100$$

for the resonant circuit of the present invention

In the case of the resonant circuit of the present invention, it applies that the efficiency and performance of the circuit since it is directly related to the voltage difference $\Delta V_C$ and not to the specific voltage values $V_{C2}$ and $V_{C3}$, also is not related to the specific values of the electric energies stored in the two energy storage devices expressed in Joules, because the electric energy stored in a capacitor with capacitance C is:

$$E_c = \frac{1}{2}CV_c^2$$

On another aspect, also the value of the total ohmic resistance R for all circuits of magnetic stimulators is an inherent characteristic of each circuit that is defined by the topology of a circuit and determined by the number of switching devices, the length of connecting cables and the other electrical components that all contribute to the increase of R. Higher values of R result in faster damping, as disclosed also from the function of $I_{L1}(t)$, and thus in higher values of % Voltage Drop. The effect of the total resistance R on the efficiency and performance of a resonant circuit of a magnetic stimulator is expressed through its contribution to the % Voltage Drop.

The % Voltage Drop constitutes the most objective value for comparing the efficiency and performance of different circuits of magnetic stimulators. For a valid comparison of different circuits, the same values of L, C and initial charging voltage must be applied. Under these conditions and for the same type of current pulses, the % Voltage Drop of each circuit accurately depicts its efficiency and performance. On the contrary, the maximum pulse repetition rate that represents the minimum time difference between two successive pulses is further dependent on the output current of the energy source, thus the maximum repetition rate is not suitable for comparing the efficiency and performance of different circuits. To elaborate further, there is the example of increasing the power input of the energy source of a magnetic stimulator circuit which for this reason the energy source outputs a higher current that charges the energy storage device faster and the maximum repetition rate is increased but due to an external of the circuit factor.

Figure 5:
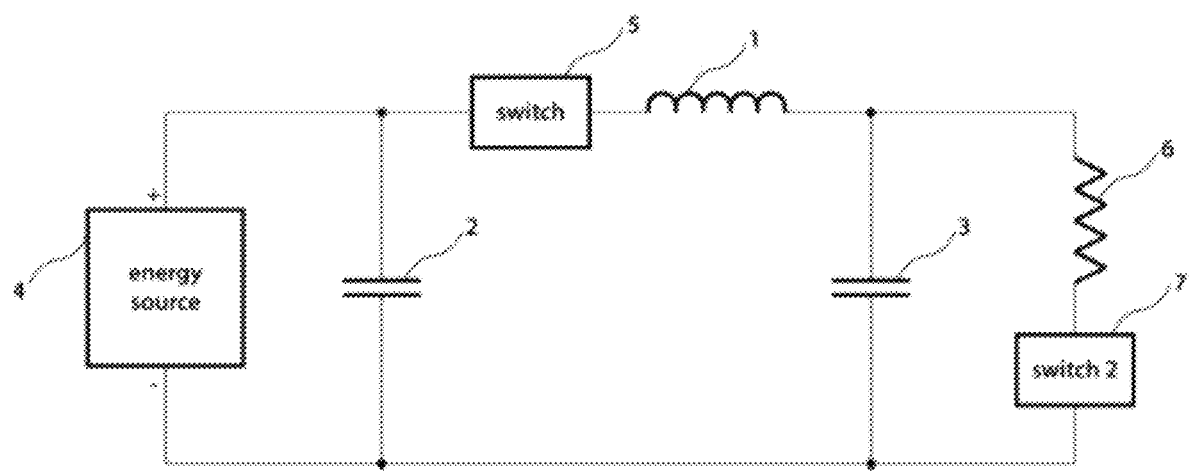
FIG. 5 is an illustrative diagram of an optional embodiment of a magnetic stimulator that is the embodiment of FIG. 1 further comprising a serial connection of a resistor and a second switch and the serial connection of the resistor and the second switch is connected in parallel to the second energy storage device.
Figure 6A:
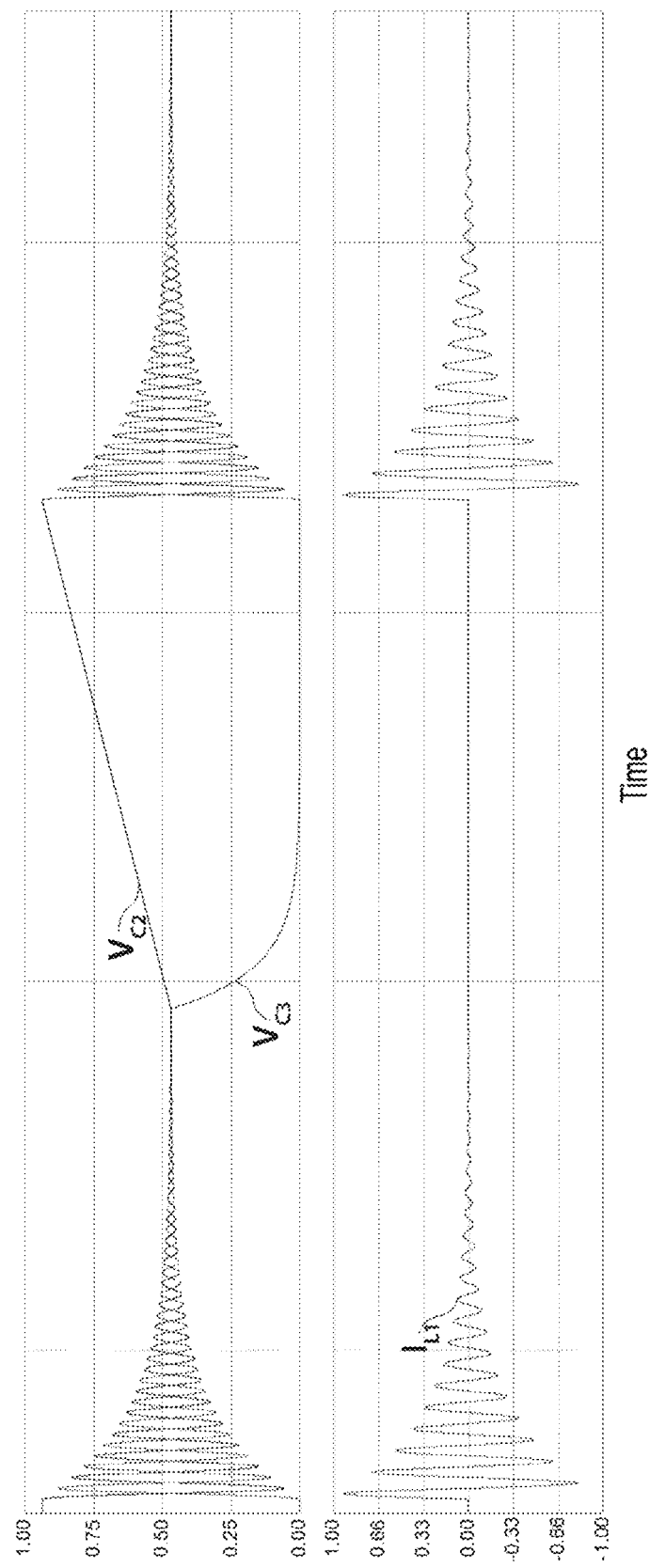
Figure 6B:
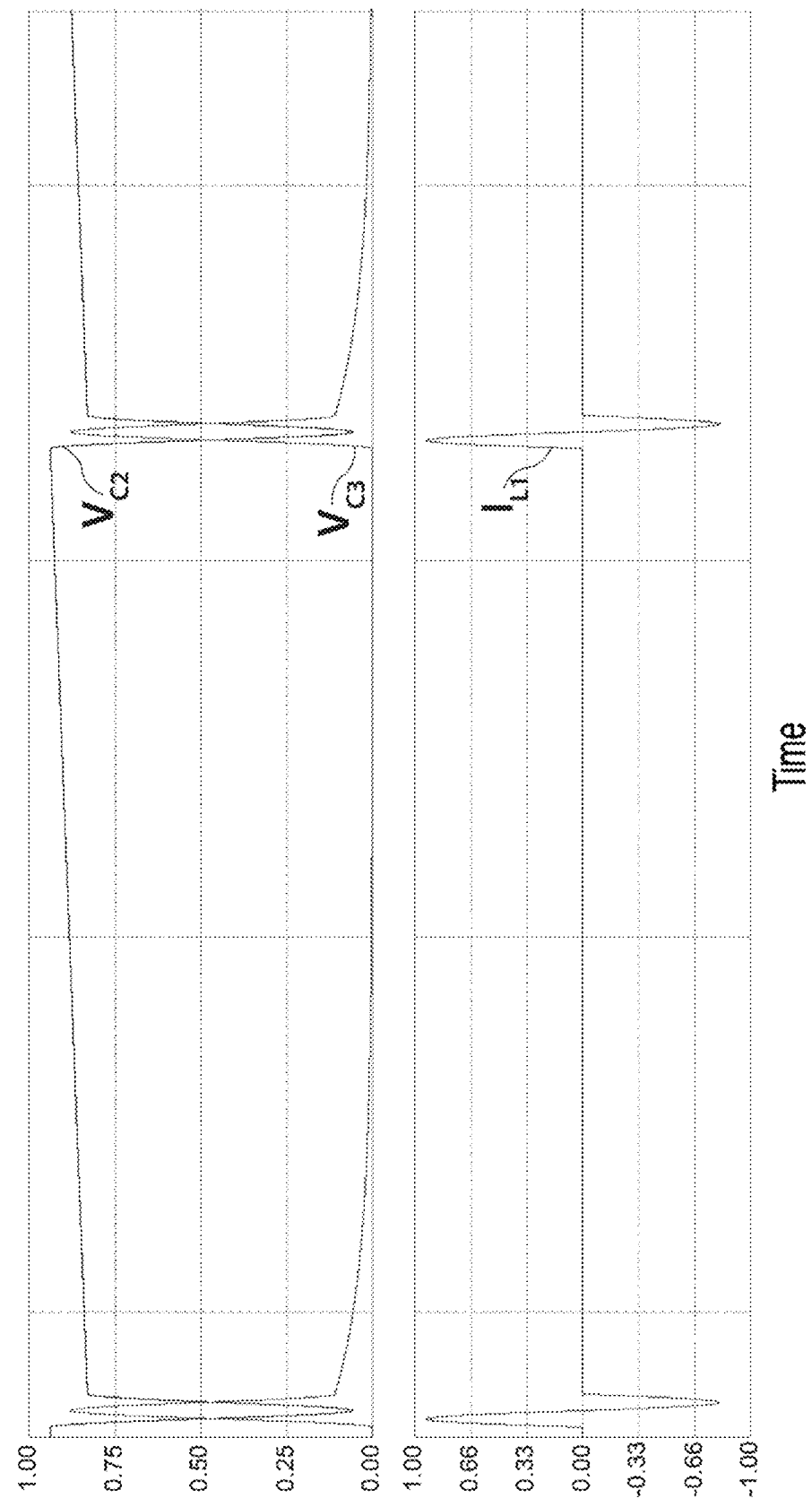
Figure 7:
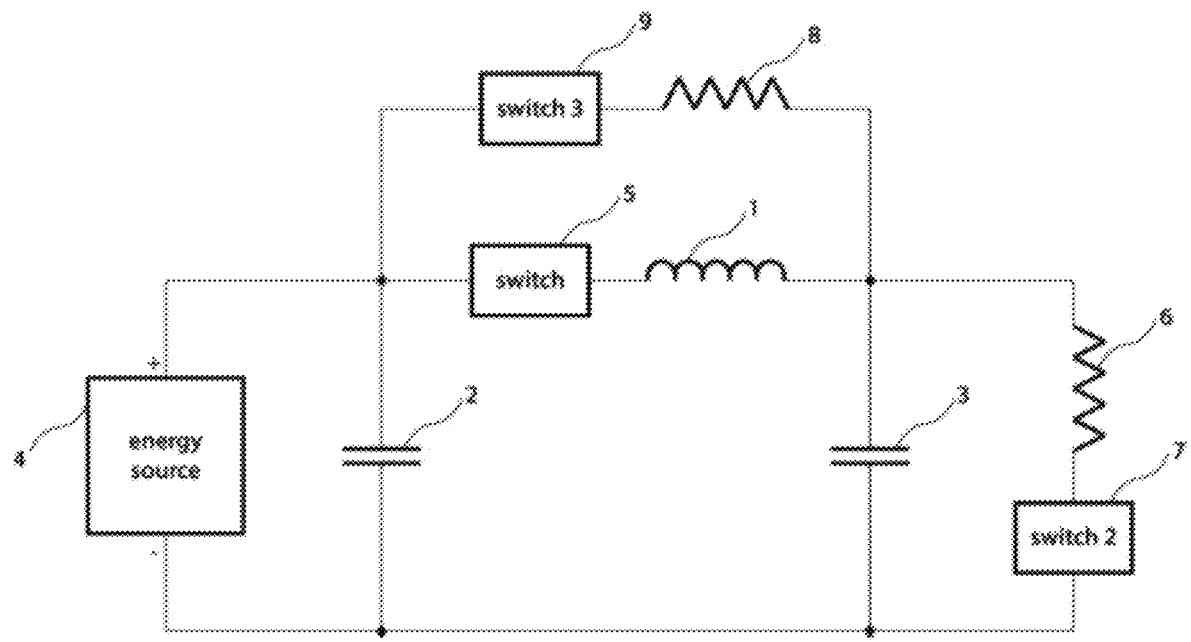
FIG. 7 is an illustrative diagram of an optional embodiment of a magnetic stimulator that is the embodiment of FIG. 5 further comprising a serial connection of a third switch and a second resistor and the serial connection of the third switch and the second resistor is connected in parallel to the serial connection of the first switch and the magnetic field generating device.
Figure 8:
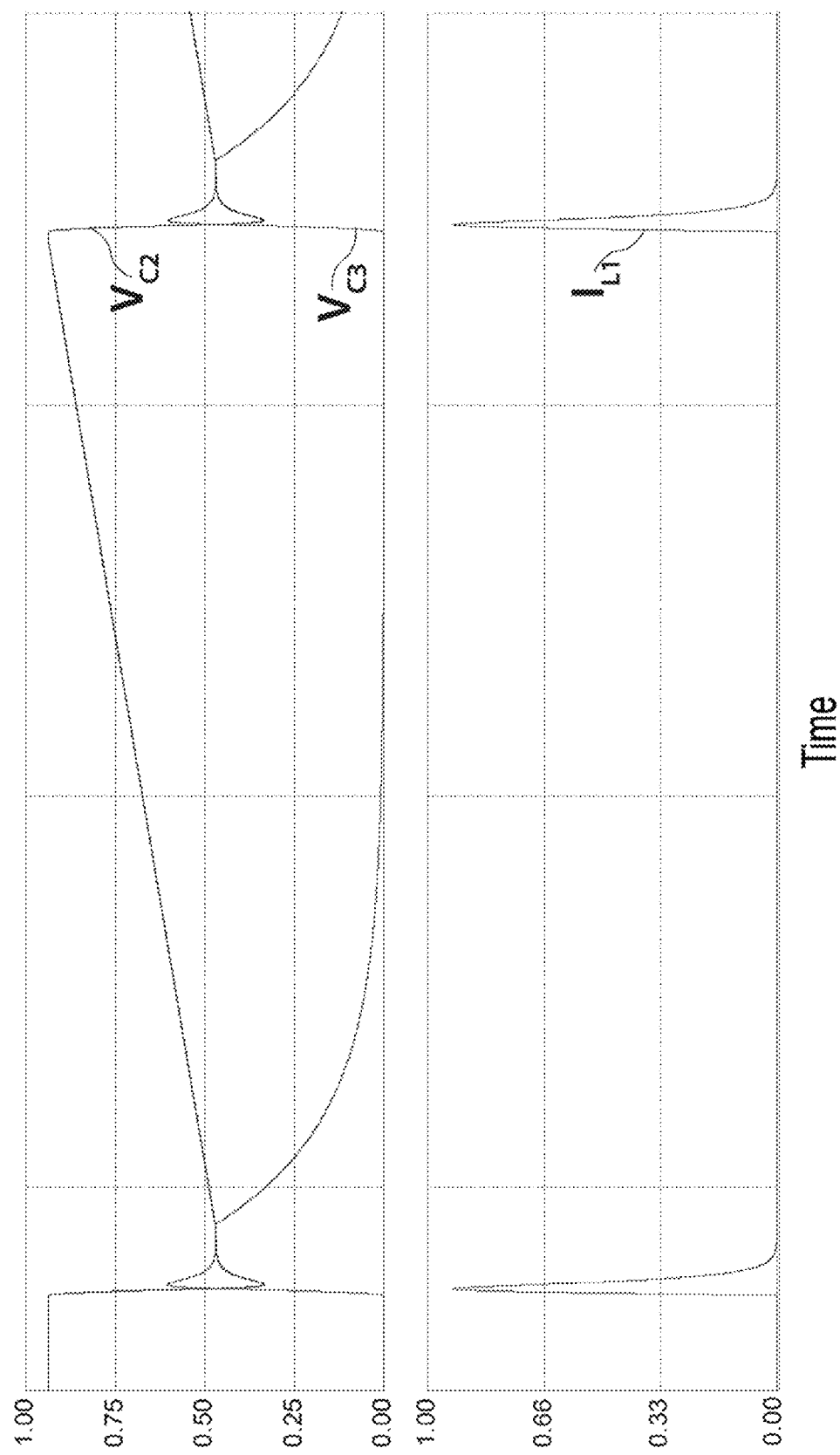
FIG. 8 is an illustrative graph of the voltages of the two energy storage devices and the current of the magnetic field generating device generated by using the embodiment of FIG. 7, showing two monophasic pulses.
Figure 9:
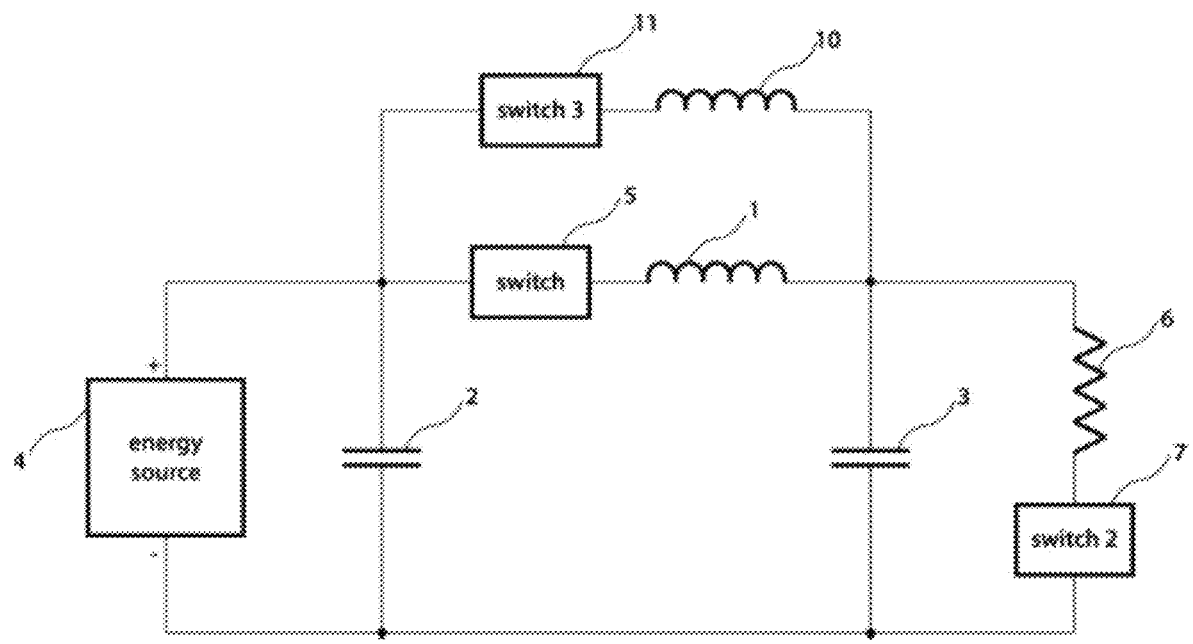
FIG. 9 is an illustrative diagram of an optional embodiment of a magnetic stimulator that is the embodiment of FIG. 5 further comprising a serial connection of a third switch and a second magnetic field generating device and the serial connection of the third switch and the second magnetic field generating device is connected in parallel to the serial connection of the first switch and the first magnetic field generating device.
Figure 10:
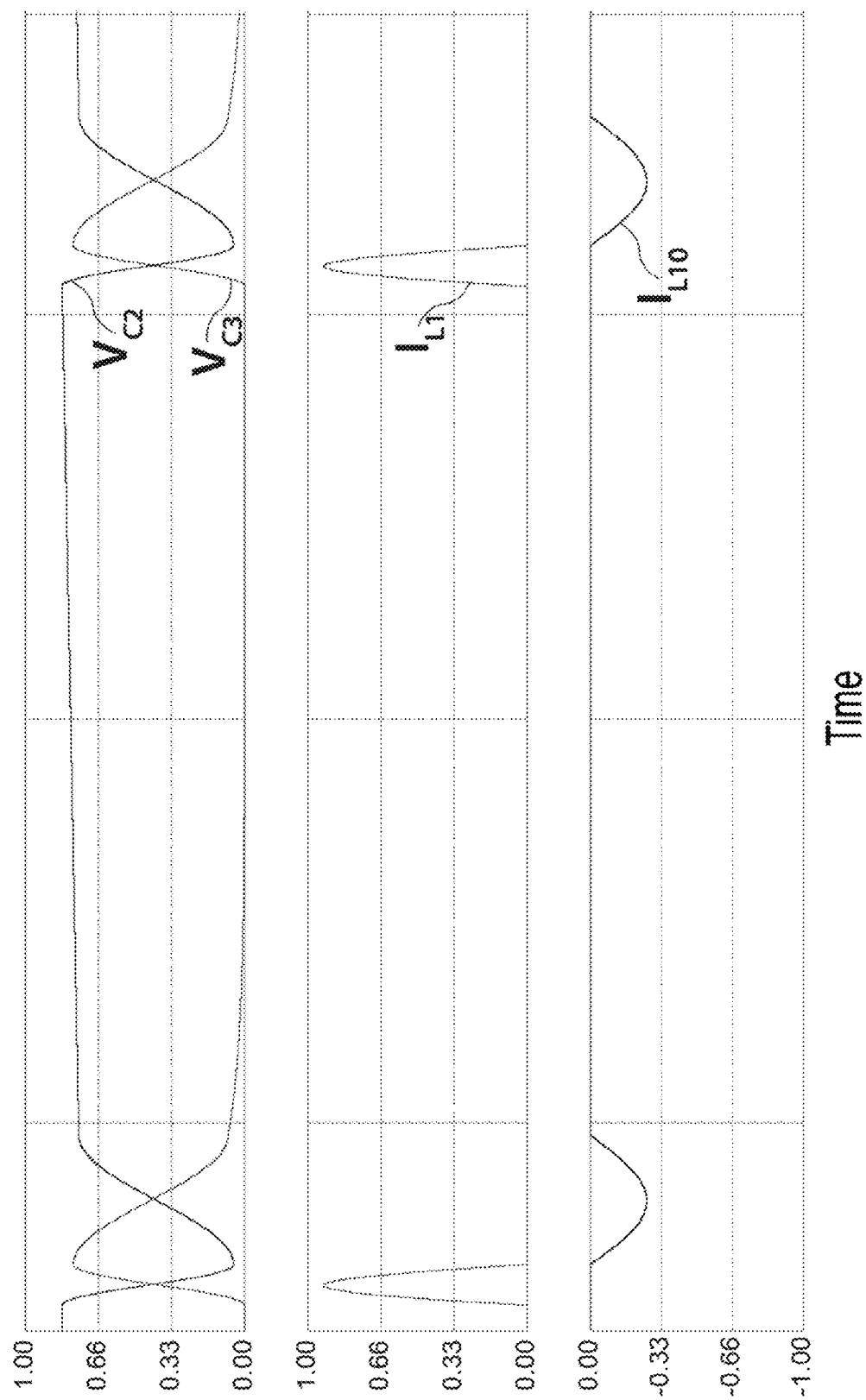
FIG. 10 is an illustrative graph of the voltages of the two energy storage devices, the current of the first magnetic field generating device and the current of the second magnetic field generating device generated by using the embodiment of FIG. 9, showing two half-sine pulses flowing through the first magnetic field generating device.

The present invention optimizes the efficiency and performance of magnetic stimulators in addition to cancelling other disadvantages of existing technology. The voltage across the terminals of each of the two energy storage devices (2) and (3) has always the same polarity, no current is flowing through the magnetic field generating device (1) during charging from the energy source (4) of the first energy storage device (2), there are no electrical means to protect the energy source (4) against reverse voltage polarity and after the initiation of the electrical oscillation of the resonant circuit the two energy storage devices (2) and (3) repetitively exchange electric charge without the operation of any switch. In regard to optimizing the efficiency and performance, and by way of example, FIG. 5 and FIG. 6A show a diagram of an optional embodiment of a magnetic stimulator and the graphs of the voltages of the two energy storage devices (2) and (3) $V_{C2}$ and $V_{C3}$ and of the current $I_{L1}$ of the magnetic field generating device (1) of this embodiment respectively for the continuous generation of polyphasic pulses with a 50% Voltage Drop. By way of example, FIG. 5 and FIG. 6B show a diagram of an optional embodiment of a magnetic stimulator and the graphs of the voltages of the two energy storage devices (2) and (3) $V_{C2}$ and $V_{C3}$ and of the current $I_{L1}$ of the magnetic field generating device (1) of this embodiment respectively for the continuous generation of biphasic pulses with a % Voltage Drop lower than 11%. By way of example, FIG. 7 and FIG. 8 show a diagram of an optional embodiment of a magnetic stimulator and the graphs of the voltages of the two energy storage devices (2) and (3) $V_{C2}$ and $V_{C3}$ and of the current $I_{L1}$ of the magnetic field generating device (1) of this embodiment respectively for the continuous generation of monophasic pulses with a 50% Voltage Drop. By way of example, FIG. 9 and FIG. 10 show a diagram of an optional embodiment of a magnetic stimulator and the graphs of the voltages of the two energy storage devices (2) and (3) $V_{C2}$ and $V_{C3}$ and of the current $I_{L1}$ of the magnetic field generating device (1) of this embodiment respectively for the continuous generation of half-sine pulses with a % Voltage Drop lower than 9%. The differentiation between the resonant circuit of the present invention where the voltage difference between the two energy storage devices (2) and (3) cause the oscillation to initiate, compared to RLC resonant circuits of other magnetic stimulators where the non-zero voltage of the one energy storage device causes the oscillation to initiate, offers a unique advantage to the present invention by adding a serial connection of a resistor (6) and a second switch (7) and the serial connection of the resistor (6) and the second switch (7) is connected in parallel to the second energy storage device (3), as shown in FIG. 5, FIG. 7, FIG. 9, FIG. 11, FIG. 12 and FIG. 20, and are configured to very rapidly discharge at the end of each pulse the remaining voltage of the second energy storage device (3). The fast discharge of the second energy storage device (3) results in increased $\Delta V_{C, end\ of\ pulse}$, which leads to reduce of the % Voltage Drop and to better efficiency and performance. The remaining voltage at the end of each pulse of the second energy storage device (3) of the present invention, in other RLC resonant circuits with one energy storage device is captured in the voltage drop of the one energy storage device at the end of each pulse and creates the need to replenish it by charging the one energy storage device instead of being able to discard it by discharging the second energy storage device (3) as it is done with the present invention. This unique feature contributes to the higher efficiency and performance of the resonant circuit of the present invention compared to RLC resonant circuits of other magnetic stimulators. Furthermore, the feature of the present invention of discharging the second energy storage device (3) at the end of each pulse, allows the continuous emission of an unlimited number of successive pulses, as in the absence of it the remaining voltage of the second energy storage device (3) at the end of each pulse is aggregated and after a number of pulses the voltages of the two energy storage devices (2) and (3) are equalized and no further pulses can be generated. Another benefit of the invention is the possibility to generate all different types of current pulses which are used in existing technology and found to be effective in magnetic stimulation studies. The different types of current pulses are the polyphasic, the biphasic, the monophasic, the half-sine, the paired- or dual-pulse polyphasic, the paired- or dual-pulse biphasic, the paired- or dual-pulse monophasic and the paired- or dual-pulse half-sine. The possibility to generate them is provided with the basic resonant circuit based on the unique inventive concept of the invention, as depicted in FIG. 1, with the addition of a least number of switches and other components and of a least complexity. The least number of switches is important to the efficiency and performance of a magnetic stimulator because each switch with typical ratings for a magnetic stimulator imports additional ohmic resistance in the range of tens of milliohms that increase the % Voltage Drop. The least complexity is important to the efficiency and performance of a magnetic stimulator due to the fact that requires less switches and less synchronization requirements for the operation of the different components.

Referring to FIG. 2A, an illustrative graph of the voltages $V_{C2}$ and $V_{C3}$ of the two energy storage devices (2) and (3) respectively and the current $I_{L1}$ of the magnetic field generating device (1), generated by using the embodiment of FIG. 1 implementing a switch (5) configured to produce polyphasic pulses, is shown. The amplitudes are normalized and one polyphasic pulse is depicted. The time axis scale is adjusted specifically for the waveforms of this graph to allow their clear disclosure and is different from the time scale of the other graphs included in the patent. For the production of polyphasic pulses, the switch (5) is configured to close at the start of each polyphasic pulse and to remain close until the end of each polyphasic pulse during which the resonant circuit freely oscillates. At the end of each polyphasic pulse, the switch (5) opens and remains open until the start of the next polyphasic pulse. At the start of each polyphasic pulse, the first energy storage device (2) is charged with an initial voltage and the second energy storage device (3) is discharged. At the end of each polyphasic pulse, the remaining voltages of the two energy storage devices (2) and (3) are equal and have a value of 50% of the initial voltage of the first energy storage device (2). After the switch (5) opens at the end of each polyphasic pulse, the energy source (4) charges again the first energy storage device (2) from the 50% of its initial voltage to 100% and the remaining voltage of the second energy storage device (3) is decreased to zero due to its internal resistance by way of example. The intensity of the stimulation can be adjusted by selectively adjusting the amplitude of the voltage of the first energy storage device (2) before the start of a polyphasic pulse. One example of implementation of the switch (5) configured to produce polyphasic pulses is a connection of a thyristor and a diode in parallel. The thyristor remains closed from the start of each polyphasic pulse until the end of each polyphasic pulse by receiving a repetitive trigger signal. At the end of each polyphasic pulse, the thyristor automatically opens because the current $I_{L1}$ is zero and the repetitive trigger signal is stopped. Other implementations may be used, consistent with the spirit of the invention.

Referring to FIG. 2B, an illustrative graph of the voltages $V_{C2}$ and $V_{C3}$ of the two energy storage devices (2) and (3) respectively and the current $I_{L1}$ of the magnetic field generating device (1), generated by using the embodiment of FIG. 1 implementing a switch (5) configured to produce biphasic pulses, is shown. The amplitudes are normalized and one biphasic pulse is depicted. The time axis scale is adjusted specifically for the waveforms of this graph to allow their clear disclosure and is different from the time scale of the other graphs included in the patent. For the production of biphasic pulses, the switch (5) is configured to close at the start of each biphasic pulse and to remain close until the end of the period $T_d$. At the start of each biphasic pulse, the first energy storage device (2) is charged with an initial voltage and the second energy storage device (3) is discharged. At $T_d/4$, the voltages $V_{C2}$ and $V_{C3}$ are equalized and have a value of 50% of the initial voltage of the first energy storage device (2), and the current $I_{L1}$ reaches its maximum positive value. At $T_d/2$ and due to losses attributed to ohmic resistance, the second energy storage device (3) is charged with a voltage equal to the initial voltage of the first energy storage device (2) minus a minimum voltage decrement and the first energy storage device (2) is not fully discharged but retains a minimum voltage increment over zero. Also at $T_d/2$, the current $I_{L1}$ has a zero value and after that it starts flowing towards the opposite direction. At $3T_d/4$, the voltages $V_{C2}$ and $V_{C3}$ are again equalized and have a value of 50% of the initial voltage of the first energy storage device (2), and the current $I_{L1}$ reaches its maximum negative value. At Ta, the two energy storage devices (2) and (3) have been charged with almost their initial values, the first energy storage device (2) with its initial voltage minus a minimum voltage decrement and the second energy storage device (3) with a minimum voltage increment over zero because of the ohmic resistance losses. At $T_d$ the biphasic pulse ends, the switch (5) opens and the energy source (4) charges again the first energy storage device (2) to its initial voltage by the requirement of replenishing only the minimum voltage decrement, whereas the minimum voltage increment over zero of the second energy storage device (3) is decreased to zero due to its internal resistance by way of example, for the next biphasic pulse to be generated. The intensity of the stimulation can be adjusted by selectively adjusting the amplitude of the voltage of the first energy storage device (2) before the start of a biphasic pulse. One example of implementation of the switch (5) configured to produce biphasic pulses is a connection of a thyristor and a diode in parallel. The thyristor closes at the start of each biphasic pulse by receiving a trigger signal and automatically opens at $T_d/2$ when the current $I_{L1}$ is zero, allowing the reverse current of the second half-period to flow through the diode. Other implementations may be used, consistent with the spirit of the invention.

Figure 2C:
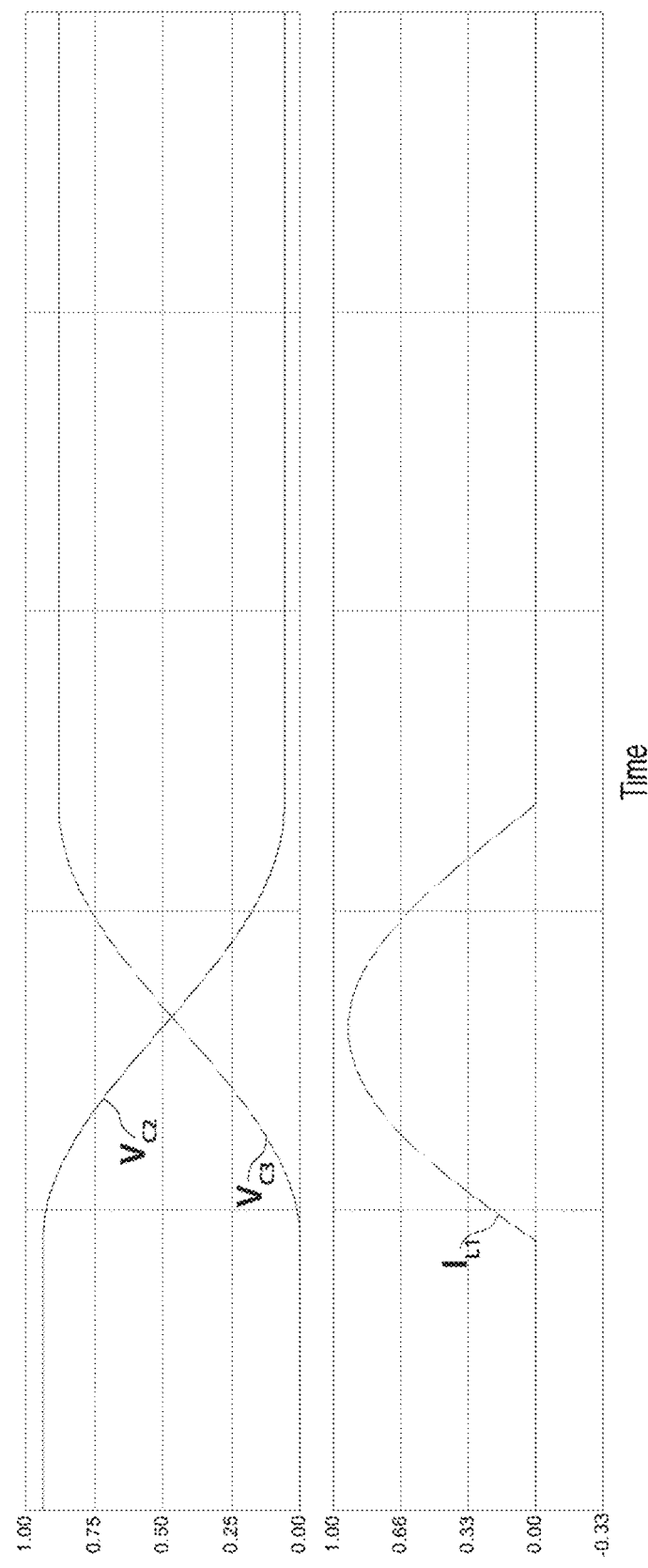

Referring to FIG. 2C, an illustrative graph of the voltages $V_{C2}$ and $V_{C3}$ of the two energy storage devices (2) and (3) respectively and the current $I_{L1}$ of the magnetic field generating device (1), generated by using the embodiment of FIG. 1 implementing a switch (5) configured to produce half-sine pulses, is shown. The amplitudes are normalized and one half-sine pulse is depicted. The time axis scale is adjusted specifically for the waveforms of this graph to allow their clear disclosure and is different from the time scale of the other graphs included in the patent. For the production of half-sine pulses, the switch (5) is configured to close at the start of each half-sine pulse and to remain close until $T_d/2$. At the start of each half-sine pulse, the first energy storage device (2) is charged with an initial voltage and the second energy storage device (3) is discharged. At $T_d/4$, the voltages $V_{C2}$ and $V_{C3}$ are equalized and have a value of 50% of the initial voltage of the first energy storage device (2), and the current $I_{L1}$ reaches its maximum positive value. At the end of each half-sine pulse at $T_d/2$ and due to losses attributed to ohmic resistance, the second energy storage device (3) is charged with a voltage equal to the initial voltage of the first energy storage device (2) minus a minimum voltage decrement and the first energy storage device (2) is not fully discharged but retains a minimum voltage increment over zero. At $T_d/2$, the current $I_{L1}$ has a zero value and the switch (5) opens so that the energy source (4) charges again the first energy storage device (2) to its initial voltage and the voltage of the second energy storage device (3) is decreased to zero due to its internal resistance by way of example, for the next half-sine pulse to be generated. The intensity of the stimulation can be adjusted by selectively adjusting the amplitude of the voltage of the first energy storage device (2) before the start of a half-sine pulse. One example of implementation of the switch (5) configured to produce half-sine pulses is a thyristor. The thyristor closes at the start of each half-sine pulse by receiving a trigger signal and automatically opens at $T_d/2$ when the current $I_{L1}$ is zero. Other implementations may be used, consistent with the spirit of the invention.

Figure 3:
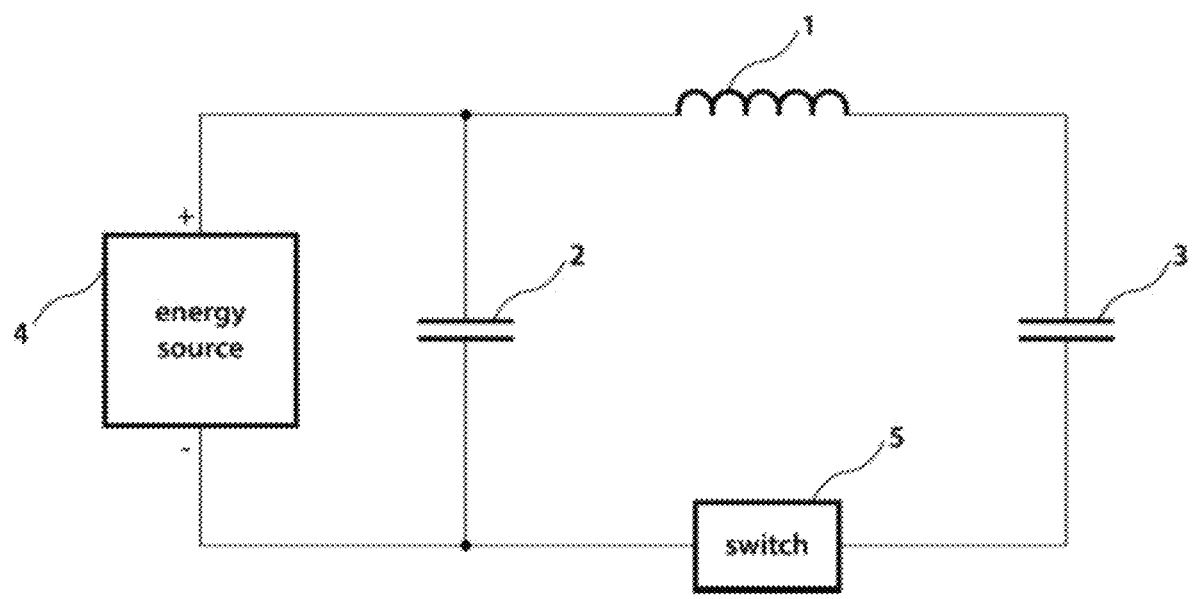
FIG. 3 illustrates a modification of the embodiment shown in FIG. 1, wherein the position of the switch is modified to being connected in series between the two energy storage devices and included in the same branch of the circuit with the second energy storage device.

Referring to FIG. 3, a modification of the embodiment shown in FIG. 1 is illustrated. The modification is the change of the position of the switch (5), which from being connected in series between the first energy storage device (2) and the magnetic field generating device (1) and included in the same branch of the circuit with the magnetic field generating device (1) in FIG. 1, is modified to being connected in series between the first energy storage device (2) and the second energy storage device (3) and included in the same branch of the circuit with the second energy storage device (3) as shown in FIG. 3. This change of the topology does not alter any of the features, the operation or the performance of the embodiment of FIG. 1, which remain the same for the embodiment of FIG. 3. Equivalent alternative embodiment of the embodiment shown in FIG. 3 with the same features, operation and performance occurs when the positions of the magnetic field generating device (1) and the switch (5) are mutually exchanged. The possibility of the embodiment of FIG. 3 to generate different types of current pulses is not restricted to the commonly used types but is extended to the generation of any arbitrary waveform of current pulse which can be generated by accordingly adjusting the selected time points of opening and closing the switch (5).

Figure 4:
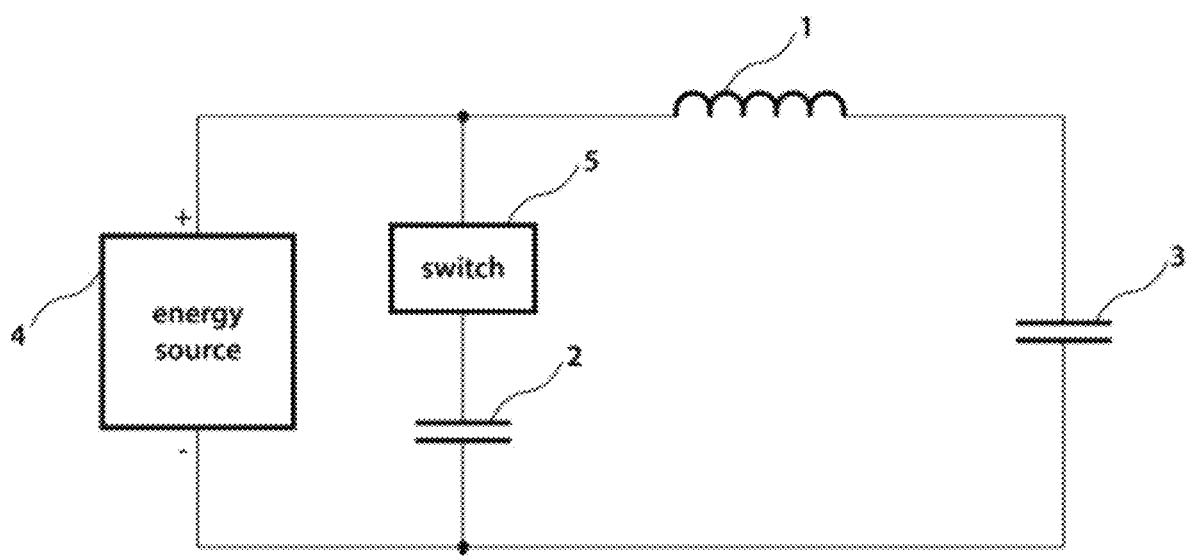
FIG. 4 illustrates another modification of the embodiment shown in FIG. 1, wherein the position of the switch is modified to being connected in series between the first energy storage device and the magnetic field generating device and included in the same branch of the circuit with the first energy storage device.

Referring to FIG. 4, another modification of the embodiment shown in FIG. 1 is illustrated. The modification is the change of the position of the switch (5), which from being connected in series between the first energy storage device (2) and the magnetic field generating device (1) and included in the same branch of the circuit with the magnetic field generating device (1) in FIG. 1, is modified to being connected in series between the first energy storage device (2) and the magnetic field generating device (1) and included in the same branch of the circuit with the first energy storage device (2) as shown in FIG. 4. This change of the topology alters the operation of the embodiment of FIG. 1 in regard to that the energy source (4) does not charge the first energy storage device (2) as it is done in the embodiment of FIG. 1 and all other embodiments deriving from the embodiment of FIG. 1, but charges the second energy storage device (3). An additional differentiation in the operation of the embodiment of FIG. 4 compared to the embodiment of FIG. 1 is that in the embodiment of FIG. 4 current is flowing through the magnetic field generating device (1) during charging of the second energy storage device (3) from the energy source (4). This poses a disadvantage in the performance of the embodiment of FIG. 4 in comparison to the performance of the embodiment of FIG. 1 because when current flows through the magnetic field generating device (1) during the charging phase of the second energy storage device (3), additional losses due to ohmic resistance during charging occur, unnecessary additional heating of the magnetic field generating device (1) is produced and greater demand for cooling, the need for reduced but still existing protective circuits for the energy source (4) is created and a magnetic field with uncommon characteristics and non-investigated effects in the field of magnetic stimulation of tissues is emitted during charging. On another aspect, the embodiment of FIG. 4 offers an advantage compared to the embodiment of FIG. 1 in the case of the generation of paired- or dual-pulses where fewer switches are required to be added to this implementation compared to the embodiment of FIG. 12 which derives from the embodiment of FIG. 1.

Figure 6D:
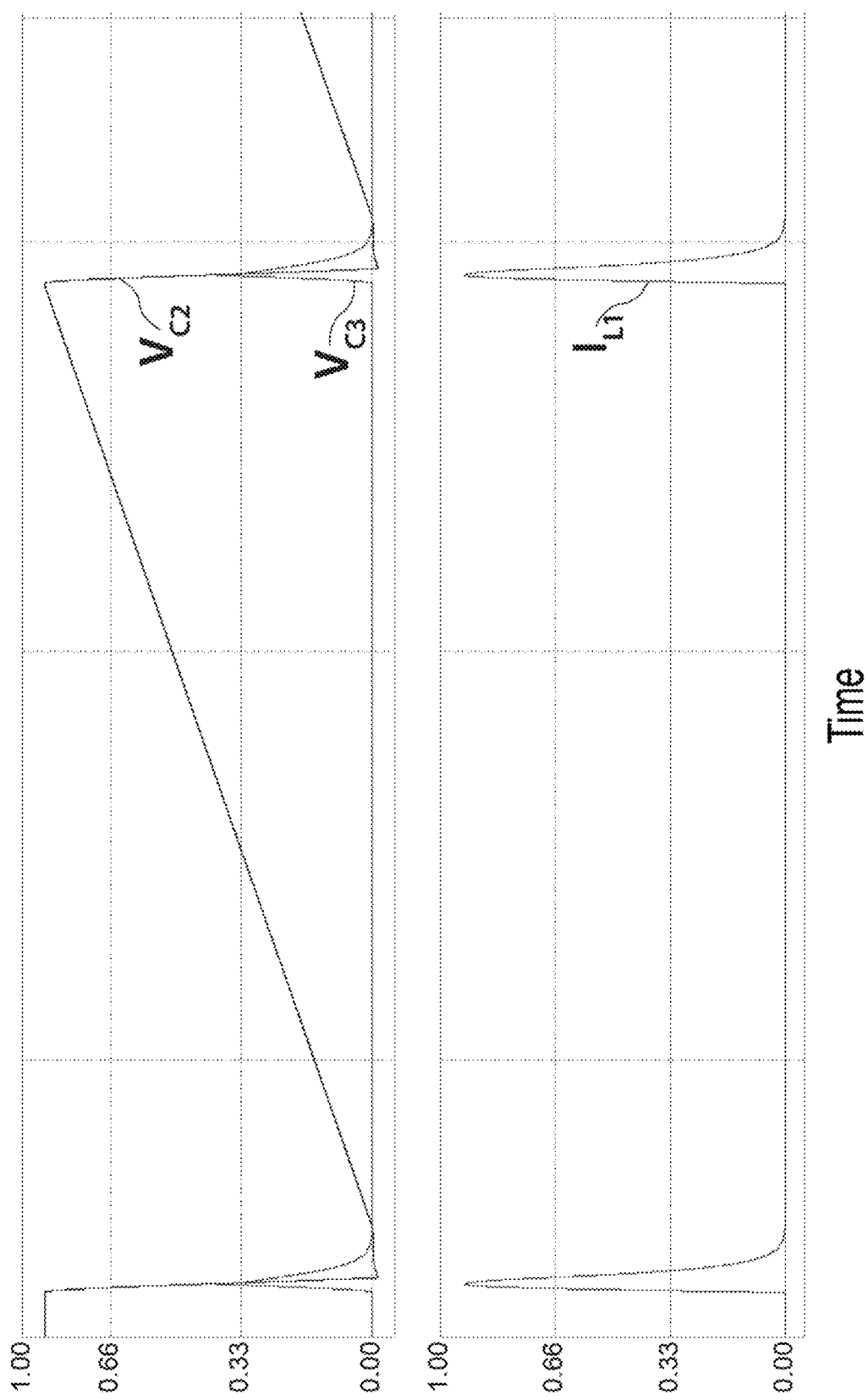

Referring to FIG. 5, an illustrative diagram of an optional embodiment of a magnetic stimulator for producing polyphasic, biphasic, half-sine and monophasic types of current pulses is shown. The embodiment of FIG. 5 is the embodiment of FIG. 1 further comprising a serial connection of a resistor (6) and a second switch (7) and the serial connection of the resistor (6) and the second switch (7) is connected in parallel to the second energy storage device (3) to selectively discharge either one of the two or both the two energy storage devices (2) and (3). This embodiment provides optimized efficiency and performance in the case of continuous generation of biphasic pulses with a % Voltage Drop lower than 11%, as depicted in FIG. 6B. Also, this embodiment provides optimized efficiency and performance in the case of continuous generation of polyphasic pulses with a 50% Voltage Drop, as depicted in FIG. 6A, due to its possibility to discard the unwanted remaining voltage of the second energy storage device (3) at the end of each polyphasic pulse by discharging the second energy storage device (3) through the resistor (6). More specifically the embodiment of FIG. 5 is the embodiment of FIG. 1 with the addition of the resistor (6) and the second switch (7) which are connected in series. The branch constituted by the serial connection of the resistor (6) and the second switch (7) is connected in parallel to the second energy storage device (3). The addition of the branch of the resistor (6) and the second switch (7) allows to selectively discharge the first energy storage device (2) or the second energy storage device (3) or both and does not differentiate the resonant circuit constituted by the first energy storage device (2), the second energy storage device (3) and the magnetic field generating device (1). The first switch (5) and the second switch (7) can be configured to independently and selectively open and close at any time point and combination so that to freely produce different shapes of current pulses, apart from the common types of current pulses. For the common types of current pulses, more specifically the advantages of the addition of the branch of the resistor (6) and the second switch (7) for each of the type of current pulses are the following. For polyphasic pulses, at the end of each polyphasic pulse the second switch (7) closes so that it allows fast discharging of the remaining 50% of the initial voltage $V_{C2}$ of the second energy storage device (3) while at the same time the first switch (5) is open so that the first energy storage device (2) is recharged from the energy source (4), as depicted in FIG. 6A. For biphasic pulses, at the end of each biphasic pulse at $T_d$ the second switch (7) closes so that it allows fast discharging of the minimum voltage increment over zero of the second energy storage device (3) while at the same time the first switch (5) is open so that the energy source (4) replenish the minimum voltage decrement of the first energy storage device (2) and recharge it back to the initial $V_{C2}$, as depicted in FIG. 6B. For half-sine pulses, at $T_d/2$ the second switch (7) closes so that it allows fast discharging of the remaining voltage of the second energy storage device (3) while at the same time the first switch (5) is open so that the first energy storage device (2) is recharged from the energy source (4), as depicted in FIG. 6C. Consequently for the cases of polyphasic, biphasic and half-sine pulses, the branch of the resistor (6) and the second switch (7) allows fast discharging of the remaining unwanted voltage of the second energy storage device (3), which contributes to increased efficiency and performance by providing lower % Voltage Drop and higher pulse repetition rates than the embodiment of FIG. 1. The resistor (6) in order to allow fast discharging has a low value of resistance, preferably in the range of few hundreds of milliohms. For monophasic pulses, at $T_d/4$ the second switch (7) closes and the first switch (5) remains closed until both the two energy storage devices (2) and (3) are fully discharged through the resistor (6) from their remaining voltages equal to the 50% of the initial voltage $V_{C2}$ resulting in a monophasic waveform current pulse, as depicted in FIG. 6D. The first switch (5) opens when the first energy storage device (2) is fully discharged so that the energy source (4) to start recharging again the first energy storage device (2) for the generation of the next monophasic pulse. On another aspect, the addition of the branch of the resistor (6) and the second switch (7) also facilitates the continuous emission of successive pulses, as in the absence of it the remaining voltage in the second energy storage device (3) at the end of each pulse is aggregated and after a number of pulses the voltages of the two energy storage devices (2) and (3) are equalized and no further pulses can be generated. The second switch (7) can be implemented with any kind of switching components or their combinations, such as thyristor, diode, IGBT, MOSFET, JFET, BJT. Other switching components may be used, consistent with the spirit of the invention. Equivalent alternative embodiments of the embodiment shown in FIG. 5 with the same features, operation and performance occur when the positions of the first switch (5) and the magnetic field generating device (1) are mutually exchanged and/or the positions of the resistor (6) and the second switch (7) are mutually exchanged. The possibility of the embodiment of FIG. 5 to generate different types of current pulses is not restricted to the commonly used types but is extended to the generation of any arbitrary waveform of current pulse which can be generated by accordingly adjusting the selected time points of opening and closing each switch.

Referring to FIG. 6A, an illustrative graph of the voltages $V_{C2}$ and $V_{C3}$ of the two energy storage devices (2) and (3) respectively and the current $I_{L1}$ of the magnetic field generating device (1), generated by using the embodiment of FIG. 5 implementing a first switch (5) and a second switch (7) configured to produce polyphasic pulses, is shown. The amplitudes are normalized and two polyphasic pulses are depicted. The time axis scale is adjusted specifically for the waveforms of this graph to allow their clear disclosure and is different from the time scale of the other graphs included in the patent. For the production of polyphasic pulses, the first switch (5) is configured to close at the start of each polyphasic pulse and to remain close until the end of each polyphasic pulse during which the resonant circuit freely oscillates. At the end of each polyphasic pulse, the first switch (5) opens and remains open until the start of the next polyphasic pulse. At the start of each polyphasic pulse, the first energy storage device (2) is charged with an initial voltage and the second energy storage device (3) is discharged. At the end of each polyphasic pulse, the remaining voltages of the two energy storage devices (2) and (3) are equal and have a value of 50% of the initial voltage of the first energy storage device (2). After the first switch (5) opens at the end of each polyphasic pulse, the energy source (4) charges again the first energy storage device (2) from the 50% of its initial voltage to 100%. The second switch (7) remains open from the start until the end of each polyphasic pulse. At the end of each polyphasic pulse, the second switch (7) closes and allows discharging of the second energy storage device (3) through the resistor (6). The second switch (7) opens again when the second energy storage device (3) is fully discharged and the current flowing through the resistor (6) and the second switch (7) is zero. The intensity of the stimulation can be adjusted by selectively adjusting the amplitude of the voltage of the first energy storage device (2) before the start of a polyphasic pulse. One example of implementation of the first switch (5) configured to produce polyphasic pulses is a connection of a thyristor and a diode in parallel. The thyristor remains closed from the start of each polyphasic pulse until the end of each polyphasic pulse by receiving a repetitive trigger signal. At the end of each polyphasic pulse, the thyristor automatically opens because current $I_{L1}$ is zero and the repetitive trigger signal is stopped. One example of implementation of the second switch (7) is a thyristor which closes at the end of each polyphasic pulse by receiving a trigger signal and remains closed until the second energy storage device (3) is fully discharged. When the second energy storage device (3) is fully discharged, the current flowing through the resistor (6) and the second switch (7) decreases to zero and the thyristor of the second switch (7) automatically opens. Other implementations for the first switch (5) and the second switch (7) may be used, consistent with the spirit of the invention.

Referring to FIG. 6B, an illustrative graph of the voltages $V_{C2}$ and $V_{C3}$ of the two energy storage devices (2) and (3) respectively and the current $I_{L1}$ of the magnetic field generating device (1), generated by using the embodiment of FIG. 5 implementing a first switch (5) and a second switch (7) configured to produce biphasic pulses, is shown. The amplitudes are normalized and two biphasic pulses are depicted. The time axis scale is adjusted specifically for the waveforms of this graph to allow their clear disclosure and is different from the time scale of the other graphs included in the patent. For the production of biphasic pulses, the first switch (5) is configured to close at the start of each biphasic pulse and to remain close until the end of the period $T_d$. At the start of each biphasic pulse, the first energy storage device (2) is charged with an initial voltage and the second energy storage device (3) is discharged. At $T_d/4$, the voltages $V_{C2}$ and $V_{C3}$ are equalized and have a value of 50% of the initial voltage of the first energy storage device (2), and the current $I_{L1}$ reaches its maximum positive value. At $T_d/2$ and due to losses attributed to ohmic resistance, the second energy storage device (3) is charged with a voltage equal to the initial voltage of the first energy storage device (2) minus a minimum voltage decrement and the first energy storage device (2) is not fully discharged but retains a minimum voltage increment over zero. Also at $T_d/2$, the current $I_{L1}$ has a zero value and after that it starts flowing towards the opposite direction. At $3T_d/4$, the voltages $V_{C2}$ and $V_{C3}$ are again equalized and have a value of 50% of the initial voltage of the first energy storage device (2), and the current $I_{L1}$ reaches its maximum negative value. At Ta, the two energy storage devices (2) and (3) have been charged with almost their initial values, the first energy storage device (2) with its initial voltage minus a minimum voltage decrement and the second energy storage device (3) with a minimum voltage increment over zero because of the ohmic resistance losses. At $T_d$ the biphasic pulse ends, the first switch (5) opens and the energy source (4) charges again the first energy storage device (2) to its initial voltage by the requirement of replenishing only the minimum voltage decrement. The second switch (7) remains open during the whole period of the biphasic pulse and at $T_d$ it closes allowing the discharge of the minimum voltage increment over zero of the second energy storage device (3) through the resistor (6). The second switch (7) opens again when the second energy storage device (3) is fully discharged and the current flowing through the resistor (6) and the second switch (7) is zero. The intensity of the stimulation can be adjusted by selectively adjusting the amplitude of the initial voltage of the first energy storage device (2) before the start of a biphasic pulse. One example of implementation of the first switch (5) configured to produce biphasic pulses is a connection of a thyristor and a diode in parallel. The thyristor closes at the start of each biphasic pulse by receiving a trigger signal and automatically opens at $T_d/2$ when the current $I_{L1}$ is zero, allowing the reverse current of the second half-period to flow through the diode. One example of implementation of the second switch (7) is a thyristor which closes at the end of each biphasic pulse by receiving a trigger signal and remains closed until the second energy storage device (3) is fully discharged. When the second energy storage device (3) is fully discharged, the current flowing through the resistor (6) and the second switch (7) decreases to zero and the thyristor of the second switch (7) automatically opens. Other implementations for the first switch (5) and the second switch (7) may be used, consistent with the spirit of the invention.

Referring to FIG. 6C, an illustrative graph of the voltages $V_{C2}$ and $V_{C3}$ of the two energy storage devices (2) and (3) respectively and the current $I_{L1}$ of the magnetic field generating device (1), generated by using the embodiment of FIG. 5 implementing a first switch (5) and a second switch (7) configured to produce half-sine pulses, is shown. The amplitudes are normalized and two half-sine pulses are depicted. The time axis scale is adjusted specifically for the waveforms of this graph to allow their clear disclosure and is different from the time scale of the other graphs included in the patent. For the production of half-sine pulses, the first switch (5) is configured to close at the start of each half-sine pulse and to remain close until $T_d/2$. At the start of each half-sine pulse, the first energy storage device (2) is charged with an initial voltage and the second energy storage device (3) is discharged. At $T_d/4$, the voltages $V_{C2}$ and $V_{C3}$ are equalized and have a value of 50% of the initial voltage of the first energy storage device (2), and the current $I_{L1}$ reaches its maximum positive value. At the end of each half-sine pulse at $T_d/2$ and due to losses attributed to ohmic resistance, the second energy storage device (3) is charged with a voltage equal to the initial voltage of the first energy storage device (2) minus a minimum voltage decrement and the first energy storage device (2) is not fully discharged but retains a minimum voltage increment over zero. At $T_d/2$, the current $I_{L1}$ has a zero value and the first switch (5) opens so that the energy source (4) charges again the first energy storage device (2) to its initial voltage. The second switch (7) remains open during the whole period of the half-sine pulse until $T_d/2$. At $T_d/2$, the second switch (7) closes allowing the discharge of the voltage of the second energy storage device (3) through the resistor (6). The second switch (7) opens again when the second energy storage device (3) is fully discharged and the current flowing through the resistor (6) and the second switch (7) is zero. The intensity of the stimulation can be adjusted by selectively adjusting the amplitude of the voltage of the first energy storage device (2) before the start of a half-sine pulse. One example of implementation of the first switch (5) configured to produce half-sine pulses is a thyristor. The thyristor closes at the start of each half-sine pulse by receiving a trigger signal and automatically opens at $T_d/2$ when the current $I_{L1}$ is zero. One example of implementation of the second switch (7) is a thyristor which closes at the end of each half-sine pulse by receiving a trigger signal and remains closed until the second energy storage device (3) is fully discharged. When the second energy storage device (3) is fully discharged, the current flowing through the resistor (6) and the second switch (7) decreases to zero and the thyristor of the second switch (7) automatically opens. Other implementations for the first switch (5) and the second switch (7) may be used, consistent with the spirit of the invention.

Referring to FIG. 6D, an illustrative graph of the voltages $V_{C2}$ and $V_{C3}$ of the two energy storage devices (2) and (3) respectively and the current $I_{L1}$ of the magnetic field generating device (1), generated by using the embodiment of FIG. 5 implementing a first switch (5) and a second switch (7) configured to produce monophasic pulses, is shown. The amplitudes are normalized and two monophasic pulses are depicted. The time axis scale is adjusted specifically for the waveforms of this graph to allow their clear disclosure and is different from the time scale of the other graphs included in the patent. At the start of each monophasic pulse, the first energy storage device (2) is charged with an initial voltage and the second energy storage device (3) is discharged. For the production of monophasic pulses, the first switch (5) is configured to close at the start of each monophasic pulse and to remain close beyond $T_d/4$ while the second switch (7) is configured to remain open from the start of each monophasic pulse and to close at $T_d/4$. At $T_d/4$, the voltages $V_{C2}$ and $V_{C3}$ are equalized and have a value of 50% of the initial voltage of the first energy storage device (2), and the current $I_{L1}$ reaches its maximum positive value. At $T_d/4$, the combination of the first switch (5) remaining closed and the second switch (7) closing impose the full discharge of both the two energy storage devices (2) and (3) from their remaining voltages equal to the 50% of the initial voltage $V_{C2}$ of the first energy storage device (2) to zero. At $T_d/4$, the current $I_{L1}$ starts decaying and its shape follows the characteristic waveform of a monophasic pulse, that being the reason for the first switch (5) to remain close at $T_d/4$ instead of opening. When both the two energy storage devices (2) and (3) are fully discharged, the first switch (5) and the second switch (7) open and the energy source (4) starts charging again the first energy storage device (2) for the generation of the next monophasic pulse. The intensity of the stimulation can be adjusted by selectively adjusting the amplitude of the voltage of the first energy storage device (2) before the start of a monophasic pulse. One example of implementation of the first switch (5) configured to produce monophasic pulses is a thyristor. The thyristor closes at the start of each monophasic pulse by receiving a trigger signal and opens automatically when the first energy storage device (2) is fully discharged and the current $I_{L1}$ is zero. One example of implementation of the second switch (7) is a thyristor which closes at $T_d/4$ by receiving a trigger signal and remains closed until both the two energy storage devices (2) and (3) are fully discharged through the resistor (6). When the two energy storage devices (2) and (3) are fully discharged, the current flowing through the resistor (6) and the second switch (7) decreases to zero and the thyristor of the second switch (7) automatically opens. Other implementations for the first switch (5) and the second switch (7) may be used, consistent with the spirit of the invention. A minimal reverse charging appearing at the first energy storage device (2) after $T_d/4$ at the end of its discharging can be eliminated if desired with the use of an additional diode connected in parallel to the first energy storage device (2).

Referring to FIG. 7, an illustrative diagram of an optional embodiment of a magnetic stimulator for producing polyphasic, biphasic, half-sine and monophasic types of current pulses is shown. The embodiment of FIG. 7 is the embodiment of FIG. 5 further comprising a serial connection of a third switch (9) and a second resistor (8) and the serial connection of the third switch (9) and the second resistor (8) is connected in parallel to the serial connection of the first switch (5) and the magnetic field generating device (1). This embodiment provides optimized efficiency and performance in the case of continuous generation of monophasic pulses with a 50% Voltage Drop, as depicted in FIG. 8. More specifically the embodiment of FIG. 7 is the embodiment of FIG. 5 with the addition of an extra circuit branch that is connected in parallel to the serial connection of the first switch (5) and the magnetic field generating device (1). This additional branch is consisted from the serial connection of the third switch (9) and the second resistor (8). The disadvantage of the embodiment of FIG. 5 in the case of the continuous generation of monophasic pulses, as shown in FIG. 6D, is the full discharge of the first energy storage device (2) which is imposed by the requirement to retain the first switch (5) closed at $T_d/4$ in order for the current $I_{L1}$ to decay through the first resistor (6) and therefore produce the characteristic waveform of a monophasic current pulse. If the first switch (5) would open at $T_d/4$ in the embodiment of FIG. 5, the $I_{L1}$ would abruptly decrease to zero producing not the characteristic waveform of a monophasic current pulse. This disadvantage of the embodiment of FIG. 5 is eliminated in the embodiment of FIG. 7 in the way of incorporating the branch of the third switch (9) and the second resistor (8) that allows the current $I_{L1}$ to decay accordingly for the production of a monophasic current pulse while the first energy storage device (2) preserves the 50% of its initial voltage which is not required to be replenished by recharging from the energy source (4) for the generation of the next monophasic pulse. At $T_d/4$, the voltages $V_{C2}$ and $V_{C3}$ of the two energy storage devices (2) and (3) respectively are equalized and have a value of 50% of the initial voltage of the first energy storage device (2) therefore no voltage difference exist to impose the current $I_{L1}$ to continue to flow on this perspective. However the $I_{L1}$ is driven to continue to flow due to the induced electromotive force applied by the decreasing magnetic field around the magnetic field generating device (1). This driven current $I_{L1}$ due to the decreasing magnetic field around the magnetic field generating device (1) at $T_d/4$ is allowed to decay through the second resistor (8) by closing the third switch (9) at $T_d/4$ and retaining the first switch (5) closed after $T_d/4$. The result of this approach is a characteristic monophasic waveform current pulse for the $I_{L1}$ to be generated and also the two energy storage devices (2) and (3) to retain their voltages equal to the 50% of the initial voltage of the first energy storage device (2). The second resistor (8) has a selected value of resistance so that the pulse duration of the monophasic pulse to correspond to the common and accepted range of duration of monophasic pulses. When $I_{L1}$ reaches zero the first switch (5) and the third switch (9) open and at that time point the second switch (7) closes allowing the discharge of the unwanted remaining voltage of the second energy storage device (3) through the first resistor (6). Consequently the energy source (4) is required to replenish the first energy storage device (2) from 50% of its initial voltage to 100% for the next monophasic pulse to follow, expressed also as a 50% Voltage Drop. The third switch (9) can be implemented with any kind of switching components or their combinations, such as thyristor, diode, IGBT, MOSFET, JFET, BJT. Other switching components may be used, consistent with the spirit of the invention. Equivalent alternative embodiments of the embodiment shown in FIG. 7 with the same features, operation and performance occur when the positions of the first switch (5) and the magnetic field generating device (1) are mutually exchanged and/or the positions of the third switch (9) and the second resistor (8) are mutually exchanged and/or the positions of the first resistor (6) and the second switch (7) are mutually exchanged. The possibility of the embodiment of FIG. 7 to generate different types of current pulses is not restricted to the commonly used types but is extended to the generation of any arbitrary waveform of current pulse which can be generated by accordingly adjusting the selected time points of opening and closing each switch.

Referring to FIG. 8, an illustrative graph of the voltages $V_{C2}$ and $V_{C3}$ of the two energy storage devices (2) and (3) respectively and the current $I_{L1}$ of the magnetic field generating device (1), generated by using the embodiment of FIG. 7 implementing a first switch (5), a second switch (7) and a third switch (9) configured to produce monophasic pulses, is shown. The amplitudes are normalized and two monophasic pulses are depicted. The time axis scale is adjusted specifically for the waveforms of this graph to allow their clear disclosure and is different from the time scale of the other graphs included in the patent. At the start of each monophasic pulse, the first energy storage device (2) is charged with an initial voltage and the second energy storage device (3) is discharged. For the production of monophasic pulses, the first switch (5) is configured to close at the start of each monophasic pulse and to remain close beyond $T_d/4$ while the third switch (9) is configured to remain open from the start of each monophasic pulse and to close at $T_d/4$ and the second switch (7) is configured to remain open from the start of each monophasic pulse and to close when the current $I_{L1}$ is equal to zero at the end of each monophasic pulse. At $T_d/4$, the voltages $V_{C2}$ and $V_{C3}$ are equalized and have a value of 50% of the initial voltage of the first energy storage device (2), and the current $I_{L1}$ reaches its maximum positive value. At $T_d/4$, the combination of the first switch (5) remaining closed and the third switch (9) closing impose the decay of the current $I_{L1}$ driven from the electromotive force due to the decreasing magnetic field around the magnetic field generating device (1) through the second resistor (8) from its maximum positive value to zero shaping the characteristic waveform of a monophasic pulse and the re-balance of the voltages $V_{C2}$ and $V_{C3}$ to the 50% of the initial voltage of the first energy storage device (2). When $I_{L1}$ is zero, the switches (5) and (9) open and the second switch (7) closes allowing the discharge of only the second energy storage device (3) from the remaining 50% of the initial voltage of the first energy storage device (2) to zero through the first resistor (6) and simultaneously the energy source (4) starts charging again the first energy storage device (2) for the generation of the next monophasic pulse. The intensity of the stimulation can be adjusted by selectively adjusting the amplitude of the voltage of the first energy storage device (2) before the start of a monophasic pulse. One example of implementation of the first switch (5) of the embodiment of FIG. 7 for the generation of monophasic pulses according to FIG. 8 is a thyristor which closes at the start of each monophasic pulse by receiving a trigger signal and opens automatically when the current $I_{L1}$ is zero. One example of implementation of the third switch (9) of the embodiment of FIG. 7 for the generation of monophasic pulses according to FIG. 8 is a thyristor which closes at $T_d/4$ by receiving a trigger signal and opens automatically when the current $I_{L1}$ is zero. One example of implementation of the second switch (7) of the embodiment of FIG. 7 for the generation of monophasic pulses according to FIG. 8 is a thyristor which closes at the end of each monophasic pulse when the current $I_{L1}$ is zero and opens automatically when the second energy storage device (3) is fully discharged and the current flowing through the first resistor (6) and the second switch (7) decreases to zero. Other implementations for the first switch (5), the second switch (7) and the third switch (9) may be used, consistent with the spirit of the invention.

Referring to FIG. 9, an illustrative diagram of an optional embodiment of a magnetic stimulator for producing polyphasic, biphasic, half-sine and monophasic types of current pulses is shown. The embodiment of FIG. 9 is the embodiment of FIG. 5 further comprising a serial connection of a third switch (11) and a second magnetic field generating device (10) and the serial connection of the third switch (11) and the second magnetic field generating device (10) is connected in parallel to the serial connection of the first switch (5) and the first magnetic field generating device (1). This embodiment provides optimized efficiency and performance in the case of continuous generation of half-sine pulses with a % Voltage Drop lower than 9%, as depicted in FIG. 10. More specifically the embodiment of FIG. 9 is the embodiment of FIG. 5 with the addition of an extra circuit branch that is connected in parallel to the serial connection of the first switch (5) and the first magnetic field generating device (1). This additional branch is consisted from the series connection of the third switch (11) and the second magnetic field generating device (10) with an inductance $L_{10}$. Two disadvantages of the embodiment of FIG. 5 in the case of the continuous generation of half-sine pulses, as shown in FIG. 6C, are the requirements at $T_d/2$ to fully recharge the first energy storage device (2) to its initial voltage from a minimum voltage increment over zero and to fully discharge the second energy storage device (3) from the initial voltage of the first energy storage device (2) minus a minimum voltage decrement, in order for the next half-sine pulse to be generated. These disadvantages of the embodiment of FIG. 5 are eliminated in the embodiment of FIG. 9 in the way of incorporating the branch of the third switch (11) and the second magnetic field generating device (10) that allow at $T_d/2$ the oscillation to continue for a second half-period but in this second half-period the magnetic field generating device that constitutes the resonant circuit with the two energy storage devices (2) and (3) is the second magnetic field generating device (10), instead of the first magnetic field generating device (1) in the first half-period, as shown in FIG. 10. This is accomplished by opening the first switch (5) and closing the third switch (11) at $T_d/2$. With this approach, during the first half-period a half-sine current pulse is generated at the first magnetic field generating device (1), which is the stimulation mean placed over the stimulation area of tissues, as depicted in the $I_{L1}$ waveform of FIG. 10 and during the second half-period the reverse current $I_{L10}$ as depicted in FIG. 10 is flowing through the second magnetic field generating device (10) which is not involved in the stimulation of the tissues. The result is at the end of the second half-period the first energy storage device (2) has a voltage almost equal to its initial voltage minus a minimum voltage decrement and the energy source (4) is required to replenish only this minimum voltage decrement and the second energy storage device (3) has a minimum voltage increment over zero which is discharged through the resistor (6), offering an % Voltage Drop lower than 9% as measured after the discharge of the second energy storage device (3) is concluded. The preferred value of the inductance $L_{10}$ of the second magnetic field generating device (10) is not to be lower than the inductance $L_1$ in order to attain lower % Voltage Drop thus higher efficiency and enhanced performance, because this facilitates at the end of the second half-period the remaining $V_{C2}$ to be as close to the initial voltage as possible and the remaining $V_{C3}$ to be as close to zero as possible. The difference between the inductances $L_1$ and $L_{10}$ differentiates the period of the resonance between the first half-period and the second half-period, the latter being longer in duration as depicted in FIG. 10. At the end of the second half-period, the third switch (11) opens when the current $I_{L10}$ is zero and the second switch (7) closes allowing the discharge of the unwanted remaining voltage of the second energy storage device (3) through the resistor (6). The third switch (11) can be can be implemented with any kind of switching components or their combinations, such as thyristor, diode, IGBT, MOSFET, JFET, BJT. Other switching components may be used, consistent with the spirit of the invention. Equivalent alternative embodiments of the embodiment shown in FIG. 9 with the same features, operation and performance occur when the positions of the first switch (5) and the first magnetic field generating device (1) are mutually exchanged and/or the positions of the third switch (11) and the second magnetic field generating device (10) are mutually exchanged and/or the positions of the resistor (6) and the second switch (7) are mutually exchanged. The possibility of the embodiment of FIG. 9 to generate different types of current pulses is not restricted to the commonly used types but is extended to the generation of any arbitrary waveform of current pulse which can be generated by accordingly adjusting the selected time points of opening and closing each switch.

Referring to FIG. 10, an illustrative graph of the voltages $V_{C2}$ and $V_{C3}$ of the two energy storage devices (2) and (3) respectively, the current $I_{L1}$ of the first magnetic field generating device (1) and the current $I_{L10}$ of the second magnetic field generating device (10), generated by using the magnetic stimulator of FIG. 9 implementing a first switch (5), a second switch (7) and a third switch (11) configured to produce half-sine pulses, is shown. The amplitudes are normalized and two half-sine pulses are depicted. The time axis scale is adjusted specifically for the waveforms of this graph to allow their clear disclosure and is different from the time scale of the other graphs included in the patent. At the start of each half-sine pulse, the first energy storage device (2) is charged with an initial voltage and the second energy storage device (3) is discharged. For the production of half-sine pulses, the first switch (5) is configured to close at the start of each half-sine pulse and to open at $T_d/2$ at the end of the first half-period while the third switch (11) is configured to remain open from the start of each half-sine pulse and to close at $T_d/2$ when $I_{L1}$ is zero. At $T_d/2$, the combination of the first switch (5) opening and the third switch (11) closing impose the resonance to continue in the second half-period through the second magnetic field generating device (10), instead of the first magnetic field generating device (1) in the first half-period. At the end of the second half-period, the third switch (11) opens when the $I_{L10}$ is zero and at that time point the second switch (7) closes until the current flow through the second switch (7) and resistor (6) reaches zero. The intensity of the stimulation can be adjusted by selectively adjusting the amplitude of the voltage of the first energy storage device (2) before the start of a half-sine pulse. One example of implementation of the first switch (5), second switch (7) and third switch (11) is with one thyristor for each switch, where each thyristor receives a trigger signal each at its appropriate time point as already stated and each thyristor automatically opens when the current flowing through it reaches zero. Other implementations for the first switch (5), the second switch (7) and the third switch (11) may be used, consistent with the spirit of the invention.

Figure 11:
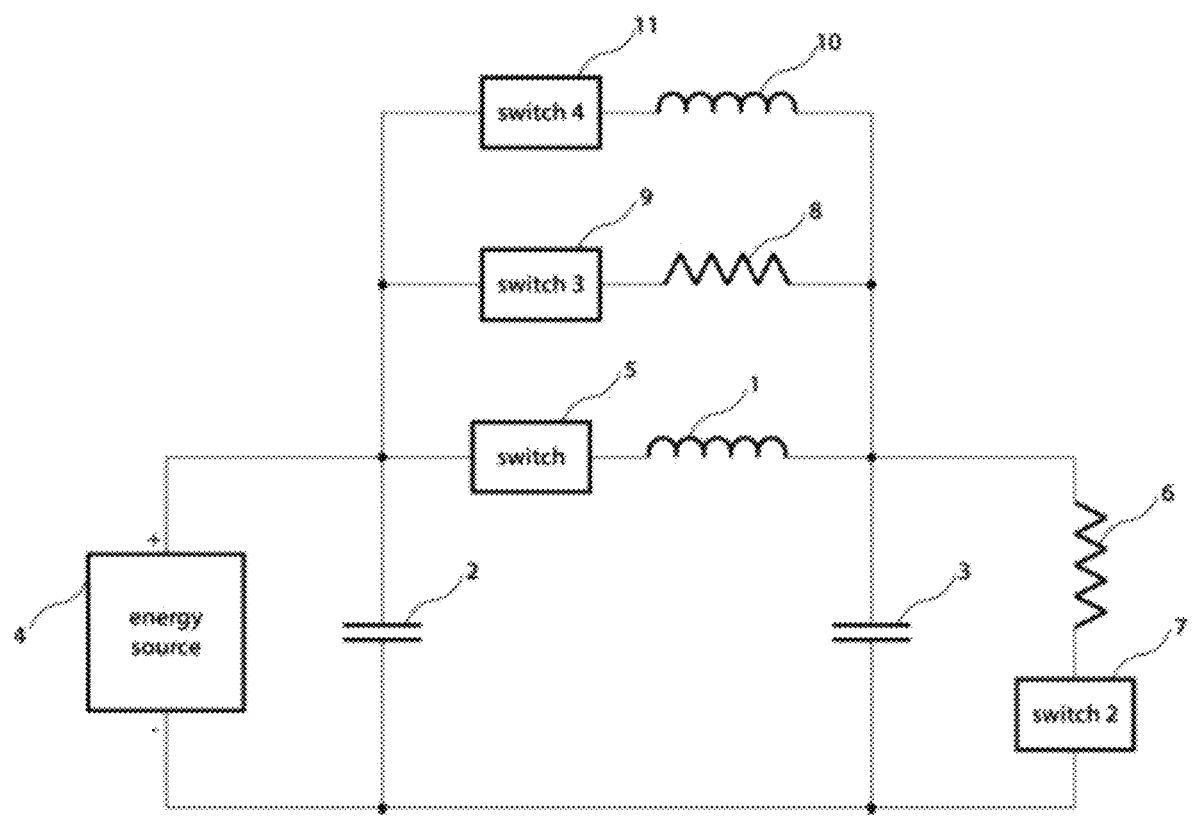
FIG. 11 is an illustrative diagram of an optional embodiment of a magnetic stimulator that is the embodiment of FIG. 5 further comprising a serial connection of a third switch and a second resistor and a serial connection of a fourth switch and a second magnetic field generating device, wherein the serial connection of the third switch and the second resistor and the serial connection of the fourth switch and the second magnetic field generating device are connected in parallel to the serial connection of the first switch and the first magnetic field generating device.

Referring to FIG. 11, an illustrative diagram of an optional embodiment of a magnetic stimulator for producing polyphasic, biphasic, half-sine and monophasic types of current pulses is shown. The embodiment of FIG. 11 is the embodiment of FIG. 5 further comprising a serial connection of a third switch (9) and a second resistor (8) and a serial connection of a fourth switch (11) and a second magnetic field generating device (10), wherein the serial connection of the third switch (9) and the second resistor (8) and the serial connection of the fourth switch (11) and the second magnetic field generating device (10) are connected in parallel to the serial connection of the first switch (5) and the first magnetic field generating device (1). This embodiment provides optimized efficiency and performance in the case of continuous generation of biphasic pulses with a % Voltage Drop lower than 11%, as depicted in FIG. 6B. Also, this embodiment provides optimized efficiency and performance in the case of continuous generation of polyphasic pulses with a 50% Voltage Drop, as depicted in FIG. 6A. Also this embodiment provides optimized efficiency and performance in the case of continuous generation of monophasic pulses with a 50% Voltage Drop, as depicted in FIG. 8. Also this embodiment provides optimized efficiency and performance in the case of continuous generation of half-sine pulses with a % Voltage Drop lower than 9%, as depicted in FIG. 10. Consequently, the embodiment of FIG. 11 provides the possibility to generate with the highest efficiency and performance any of the four common types of current pulses and any combination of them by requiring a minimum number of four switches and a minimum complexity with minimized losses due to ohmic resistance and minimized synchronization requirements. More specifically the embodiment of FIG. 11 is the embodiment of FIG. 5 with the addition of a first extra circuit branch that is connected in parallel to the serial connection of the first switch (5) and the first magnetic field generating device (1) and a second extra circuit branch that is connected in parallel to the series connection of the first switch (5) and the first magnetic field generating device (1). The first additional branch is consisted from the serial connection of the third switch (9) and the second resistor (8). The second additional branch is consisted from the serial connection of the fourth switch (11) and the second magnetic field generating device (10) with an inductance $L_{10}$. The features, operation and performance of the embodiment of FIG. 11 are equivalent for the continuous generation of polyphasic and biphasic types of current pulses to the embodiment of FIG. 5, for the continuous generation of monophasic type of current pulses to the embodiment of FIG. 7 and for the continuous generation of half-sine type of current pulses to the embodiment of FIG. 9. The only differentiation for generating the different types of current pulses are the time points of opening and closing the switching devices which follow the analyses of the embodiments of FIG. 5, FIG. 7 and FIG. 9 for each type of current pulses respectively. The possibility of the embodiment of FIG. 11 to generate different types of current pulses is not restricted to the commonly used types but is extended to the generation of any arbitrary waveform of current pulse which can be generated by accordingly adjusting the selected time points of opening and closing each switch.

Figure 12:
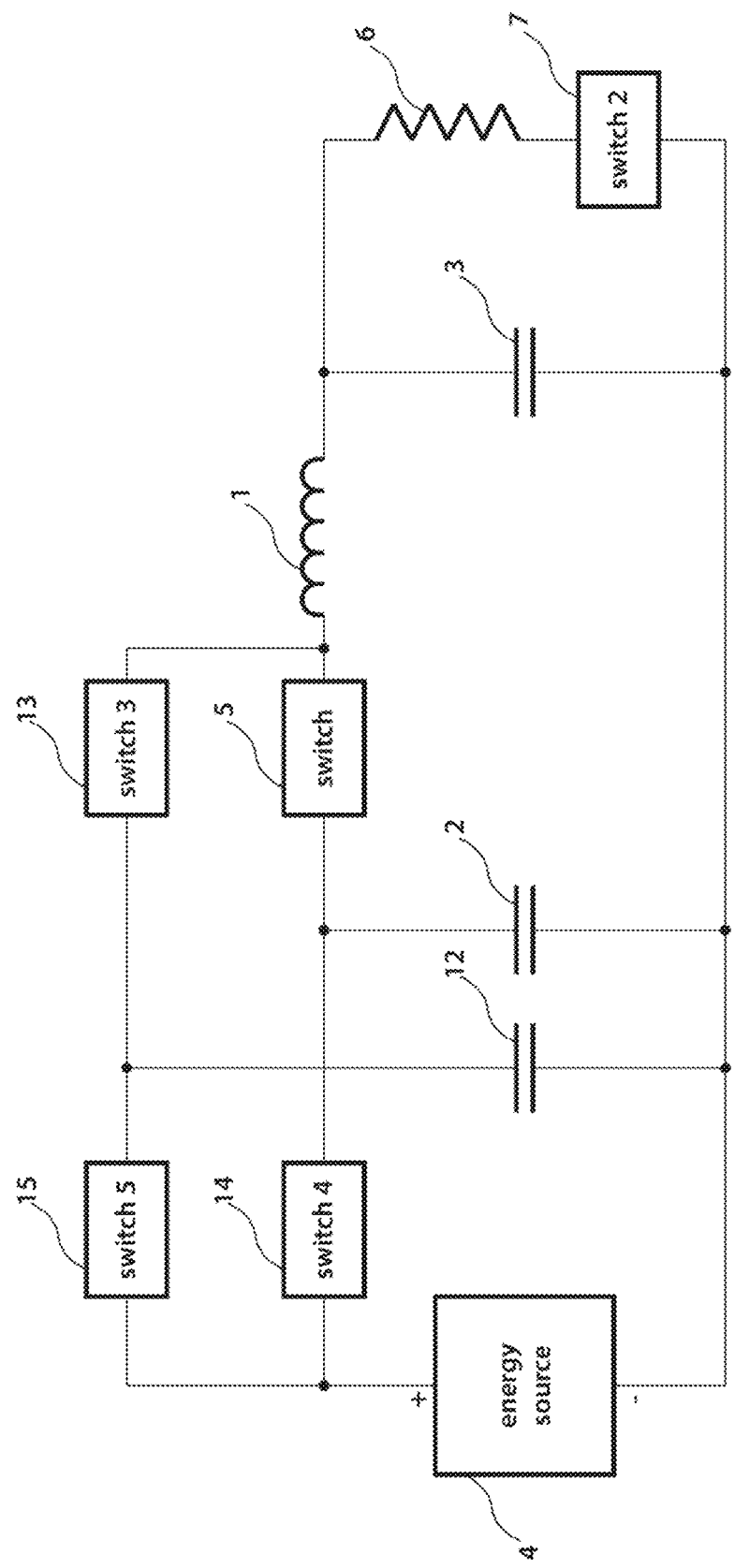
FIG. 12 is an illustrative diagram of an optional embodiment of a magnetic stimulator that is the embodiment of FIG. 5 further comprising a serial connection of a third energy storage device and a third switch and the serial connection of the third energy storage device and the third switch is connected in parallel to the serial connection of the magnetic field generating device and the second energy storage device and a fourth switch coupled between the energy source and the first energy storage device and a fifth switch coupled between the energy source and the third energy storage device.

Referring to FIG. 12, an illustrative diagram of an optional embodiment of a magnetic stimulator for producing paired- or dual-pulse polyphasic, paired- or dual-pulse biphasic, paired- or dual-pulse monophasic, paired- or dual-pulse half-sine, single-pulse of higher amplitude polyphasic, single-pulse of higher amplitude biphasic, single-pulse of higher amplitude monophasic and single-pulse of higher amplitude half-sine types of current pulses is shown. The embodiment of FIG. 12 is the embodiment of FIG. 5 further comprising a serial connection of a third energy storage device (12) and a third switch (13) and the serial connection of the third energy storage device (12) and the third switch (13) is connected in parallel to the serial connection of the magnetic field generating device (1) and the second energy storage device (3), wherein the third energy storage device (12) is further coupled to the energy source (4); and a fourth (14) and a fifth (15) switch to allow the energy source (4) to selectively charge either only the first energy storage device (2) or only the third energy storage device (12) or both, to produce pairs of current pulses of the same or different type, or single-pulses of higher amplitude of any type. This embodiment provides optimized efficiency and performance in the case of continuous generation of paired- or dual-pulse polyphasic, paired- or dual-pulse biphasic, single-pulse of higher amplitude polyphasic and single-pulse of higher amplitude biphasic types of current pulses. More specifically the embodiment of FIG. 12 is the embodiment of FIG. 5 further comprising the serial connection of the third energy storage device (12) and the third switch (13) which serial connection of the third energy storage device (12) and the third switch (13) is connected in parallel to the serial connection of the magnetic field generating device (1) and the second energy storage device (3), wherein the first switch (5) is positioned outside of the closed path of the third energy storage device (12), the third switch (13), the magnetic field generating device (1) and the second energy storage device (3) and the third energy storage device (12) is further connected in parallel to the energy source (4); and the fourth switch (14) and the fifth switch (15) coupled so that the energy source (4) to selectively charge either only the first energy storage device (2) or only the third energy storage device (12) or both. The third energy storage device (12) has a capacitance $C_{12}$ where, by way of example, the capacitance $C_{12}$ is equal to the capacitances $C_2$ and $C_3$. The selectable operation of the first switch (5) and the third switch (13) allow the embodiment to emit a first current pulse of any type due to the oscillation of the resonant circuit constituted by the first energy storage device (2), the second energy storage device (3) and the magnetic field generating device (1), followed by the discharge of the second energy storage device (3) through the branch of the resistor (6) and the second switch (7) and after these events a second current pulse of any type to be emitted due to the oscillation of the resonant circuit constituted by the third energy storage device (12), the second energy storage device (3) and the magnetic field generating device (1), followed again by the discharge of the second energy storage device (3) through the branch of the resistor (6) and the second switch (7). The first and second current pulses constitute one pair- or dual-pulse. The first and second pulse can be of any type, can be of the same type or of a different type, the choices of which depend on the selected time points of opening and closing the first switch (5) and the second switch (7) during the first current pulse and on the selected time points of opening and closing the third switch (13) and the second switch (7) during the second current pulse. The time interval between the first and second pulse is selectable and is adjusted by the time point of closing the third switch (13) after the discharge of the second energy storage device (3) after the end of the first pulse. The addition of the fourth switch (14) and the fifth switch (15) serve two different purposes. The first purpose is not allowing the short-circuiting of the first energy storage device (2) and the third energy storage device (12) that would result in an equivalent energy storage device with a capacitance being the sum of the capacitances of the first energy storage device (2) and the third energy storage device (12) connected in parallel and thus not being able to generate paired- or dual-pulses. This first purpose is achieved by avoiding the fourth switch (14) and the fifth switch (15) to be simultaneously closed during oscillation while also avoiding the first switch (5) and the third switch (13) to be simultaneously closed during oscillation. The second purpose is to provide the possibility to independently select the amplitudes of the first and the second pulse of a paired- or dual-pulse. This second purpose is achieved by retaining closed simultaneously but for different durations the fourth switch (14) and the fifth switch (15) during the charging phase by the energy source (4) of the first energy storage device (2) and of the third energy storage device (12) respectively during which phase the first switch (5) and the third switch (13) remain open. For the generation of single-pulses of higher amplitude the fourth switch (14) and the fifth switch (15) remain closed simultaneously for the same duration during the charging phase by the energy source (4) of the first energy storage device (2) and of the third energy storage device (12) respectively during which phase the first switch (5) and the third switch (13) remain open. During the oscillation phase in the case of generation of single-pulses of higher amplitude the first switch (5) and the third switch (13) close and open simultaneously for the same durations and the fourth switch (14) and the fifth switch (15) remain open. A single-pulse of higher amplitude current pulse of any type compared to the first or second current pulse of a paired- or dual-pulse of the same type has a higher maximum value of amplitude, the same maximum value of rate of change, a longer pulse duration and the working voltage rating is increased. By way of example, the embodiment of FIG. 12 can be extended to implement additional energy storage devices and switches on a similar approach to the third energy storage device (12), the third switch (13) and the fifth switch (15) for the generation of a plurality of successive pulses instead of a pair of pulses generated with the embodiment of FIG. 12. All switches can be can be implemented with any kind of switching components or their combinations, such as thyristor, diode, IGBT, MOSFET, JFET, BJT. Other switching components may be used, consistent with the spirit of the invention. Equivalent alternative embodiment of the embodiment shown in FIG. 12 with the same features, operation and performance occurs when the positions of the resistor (6) and the second switch (7) are mutually exchanged. The possibility of the embodiment of FIG. 12 to generate different types of current pulses is not restricted to the commonly used types but is extended to the generation of any arbitrary waveform of current pulse which can be generated by accordingly adjusting the selected time points of opening and closing each switch.

Figure 13:
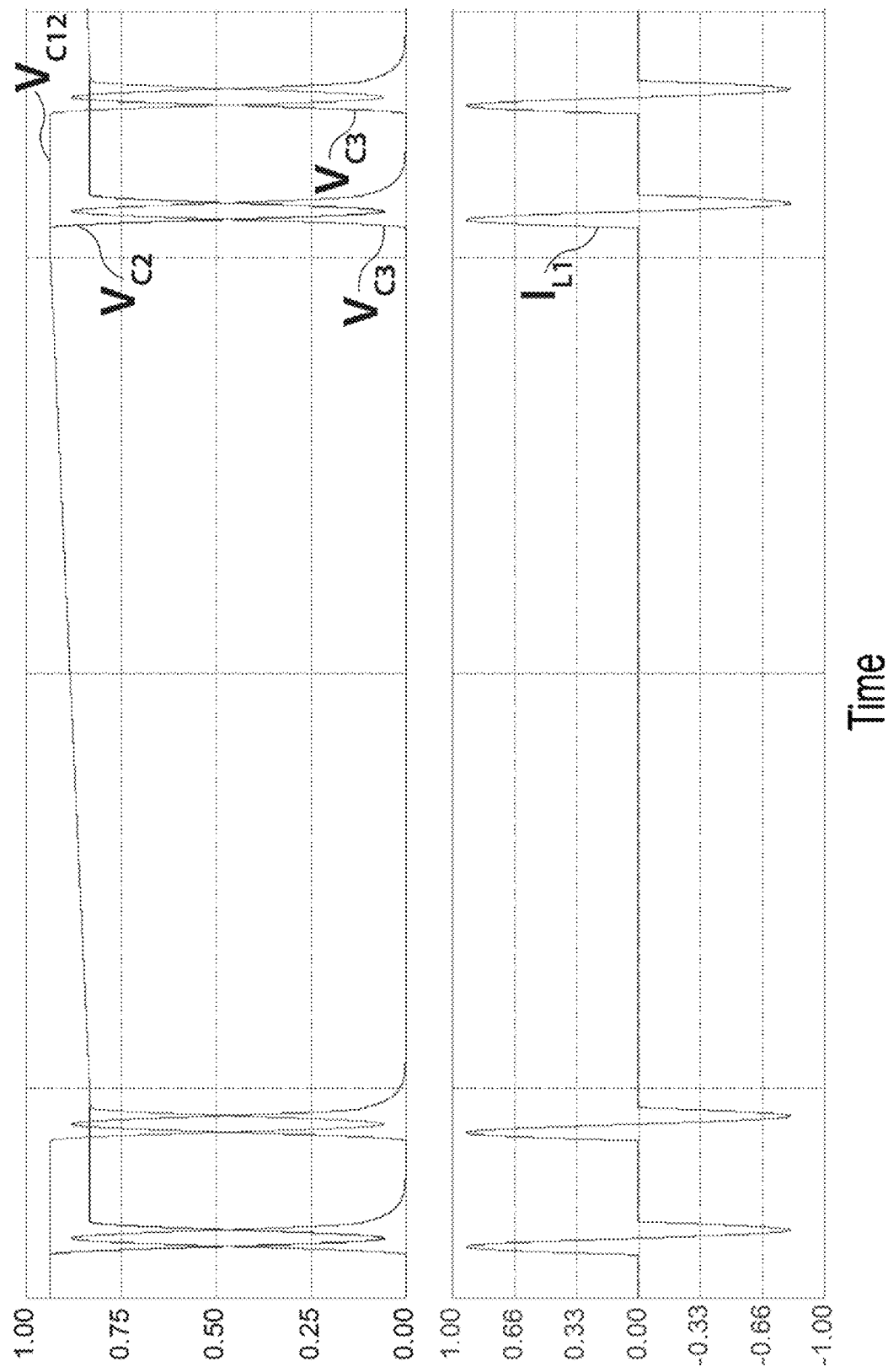
FIG. 13 is an illustrative graph of the voltages of the three energy storage devices and the current of the magnetic field generating device generated by using the embodiment of FIG. 12, showing two pairs of biphasic pulses.

Referring to FIG. 13, an illustrative graph of the voltages $V_{C2}$, $V_{C3}$ and $V_{C12}$ of the three energy storage devices (2), (3) and (12) respectively and the current $I_{L1}$ of the magnetic field generating device (1), generated by using the embodiment of FIG. 12 implementing a first switch (5), a second switch (7), a third switch (13), a fourth switch (14) and a fifth switch (15) configured to produce paired- or dual-pulse biphasic pulses, is shown. The amplitudes are normalized and two pairs of biphasic pulses are depicted where each pair consists of a first and a second biphasic pulse. The time axis scale is adjusted specifically for the waveforms of this graph to allow their clear disclosure and is different from the time scale of the other graphs included in the patent. Before the start of each pair of biphasic pulses the first energy storage device (2) and the third energy storage device (12) are charged with initial voltages, the second energy storage device (3) is discharged and all switches are open. By way of example in FIG. 13 the initial voltages of the first energy storage device (2) and the third energy storage device (12) are equal and therefore lead to the generation of two identical biphasic current pulses in each pair. The equal initial voltages of the graph in FIG. 13 occur by simultaneously closing and then opening for the same duration the fourth switch (14) and the fifth switch (15) in order for the energy source (4) to equally charge the first energy storage device (2) and the third energy storage device (12) after a pair of biphasic pulses ends and before the next pair of biphasic pulses starts. In other cases where it is desired for the two biphasic pulses of a pair to have different amplitudes of certain values, this is accomplished by independently selecting the initial voltages of the first energy storage device (2) and of the third energy storage device (12) via closing and opening the fourth switch (14) and the fifth switch (15) for different durations during the charging phase. Before the start of the first biphasic pulse of a pair and after the first energy storage device (2) and the third energy storage device (12) are charged with their initial voltages, all switches are open. At the start of the first biphasic pulse of a pair the first switch (5) closes and remains closed for one resonant period until the end of the first biphasic pulse of a pair at which time point the first switch (5) opens and the $I_{L1}$ is zero. During the period of the first biphasic pulse of a pair, the third switch (13) remains open. The period of the first biphasic pulse of a pair refers to the period of the resonant circuit which is constituted by the first energy storage device (2), the magnetic field generating device (1) and the second energy storage device (3). At the end of the first biphasic pulse of a pair, the first switch (5) opens and the second switch (7) closes until the second energy storage device (3) is fully discharged through the resistor (6). When the second energy storage device (3) is fully discharged the second switch (7) opens. After the selected time interval between the first and the second biphasic pulses of a pair has passed, the third switch (13) closes and remains closed for one resonant period until the end of the second biphasic pulse of a pair at which time point the third switch (13) opens and the $I_{L1}$ is zero. During the period of the second biphasic pulse of a pair, the switch (5) remains open. The period of the second biphasic pulse of a pair refers to the period of the resonant circuit which is constituted by the third energy storage device (12), the magnetic field generating device (1) and the second energy storage device (3). At the end of the second biphasic pulse of a pair, the third switch (13) opens and the second switch (7) closes until the second energy storage device (3) is fully discharged through the resistor (6). When the second energy storage device (3) is fully discharged the second switch (7) opens. Before the start of each pair of biphasic pulses the fourth switch (14) and the fifth switch (15) are open and remain open until the end of the second biphasic pulse of a pair, at which time point the fourth switch (14) and the fifth switch (15) close so that the first energy storage device (2) and the third energy storage device (12) are charged from the energy source (4). When charging of the first energy storage device (2) and the third energy storage device (12) is achieved, the fourth switch (14) and the fifth switch (15) open. One example of implementation of the fourth switch (14) and the fifth switch (15) is with one IGBT for each switch, where each IGBT receives a control signal with a duration equal to the desired duration for the IGBT to conduct. One example of implementation of the second switch (7) is with one thyristor, where the thyristor receives a trigger signal at its appropriate time points as already stated and the thyristor automatically opens when the current flowing through it reaches zero. One example of implementation of the first switch (5) and the third switch (13) is with a thyristor and diode in parallel for each switch, where each thyristor closes at the start of each biphasic pulse of a pair by receiving a trigger signal and automatically opens at the half-period of the same biphasic pulse when the current $I_{L1}$ is zero, allowing the reverse current of the second half-period to flow through the diode. Other implementations may be used, consistent with the spirit of the invention.

Figure 14:
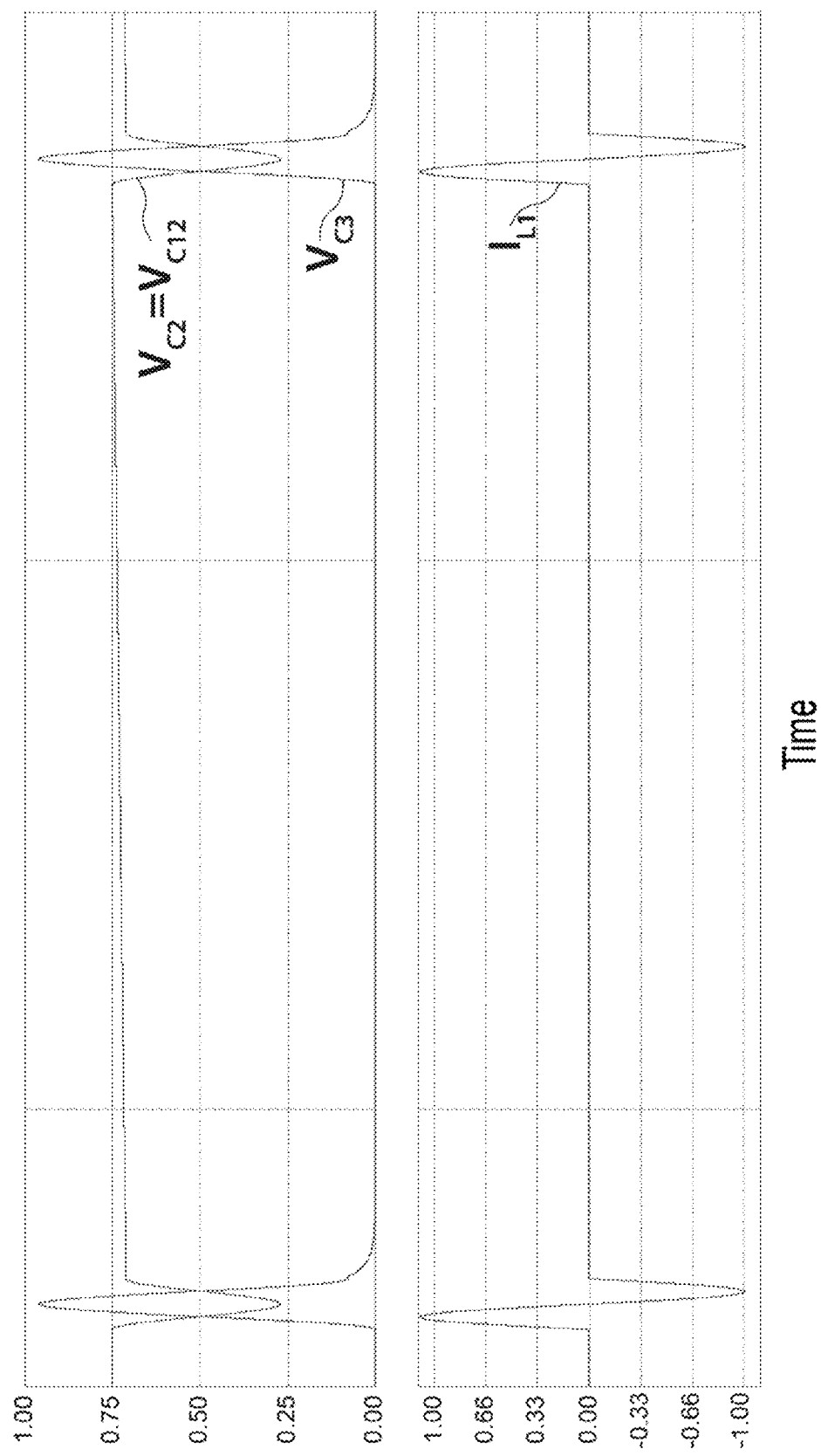
FIG. 14 is an illustrative graph of the voltages of the three energy storage devices and the current of the magnetic field generating device generated by using the embodiment of FIG. 12, showing two single-pulses of higher amplitude of biphasic type.

Referring to FIG. 14, an illustrative graph of the voltages $V_{C2}$, $V_{C3}$ and $V_{C12}$ of the three energy storage devices (2), (3) and (12) respectively and the current $I_{L1}$ of the magnetic field generating device (1), generated by using the embodiment of FIG. 12 implementing a first switch (5), a second switch (7), a third switch (13), a fourth switch (14) and a fifth switch (15) configured to produce single-pulses of higher amplitude of biphasic type, is shown. The amplitudes are normalized and two single-pulses of higher amplitude of biphasic type are depicted. The time axis scale is adjusted specifically for the waveforms of this graph to allow their clear disclosure and is different from the time scale of the other graphs included in the patent. Before the start of each single-pulse of higher amplitude of biphasic type the first energy storage device (2) and the third energy storage device (12) are charged with initial voltages, the second energy storage device (3) is discharged and all switches are open. By way of example in FIG. 14 the initial voltages of the first energy storage device (2) and of the third energy storage device (12) are equal and occur by simultaneously closing and then opening for the same duration the fourth switch (14) and the fifth switch (15) in order for the energy source (4) to equally charge the first energy storage device (2) and the third energy storage device (12) after a single-pulse of higher amplitude of biphasic type ends and before the next single-pulse of higher amplitude of biphasic type starts. Before the start of each single-pulse of higher amplitude of biphasic type and after the first energy storage device (2) and the third energy storage device (12) are charged with their initial voltages, all switches are open. At the start of each single-pulse of higher amplitude of biphasic type the first switch (5) and the third switch (13) simultaneously close and remain closed for one resonant period until the end of the single-pulse of higher amplitude of biphasic type at which time point the first switch (5) and the third switch (13) open and the $I_{L1}$ is zero. During the period of each single-pulse of higher amplitude of biphasic type, the fourth switch (14) and the fifth switch (15) remain open. The period of each single-pulse of higher amplitude of biphasic type refers to the period of the resonant circuit which is constituted by the equivalent energy storage device with a capacitance being the sum of the capacitances of the first energy storage device (2) and of the third energy storage device (12) connected in parallel, the magnetic field generating device (1) and the second energy storage device (3). At the end of each single-pulse of higher amplitude of biphasic type, the first switch (5) and the third switch (13) open and the second switch (7) closes until the second energy storage device (3) is fully discharged through the resistor (6). When the second energy storage device (3) is fully discharged the second switch (7) opens. Before the start of each single-pulse of higher amplitude of biphasic type the fourth switch (14) and the fifth switch (15) are open and remain open until the end of the single-pulse of higher amplitude of biphasic type, at which time point the fourth switch (14) and the fifth switch (15) close so that the first energy storage device (2) and the third energy storage device (12) are charged from the energy source (4). When charging of the first energy storage device (2) and of the third energy storage device (12) is achieved, the fourth switch (14) and the fifth switch (15) open. One example of implementation of the fourth switch (14) and the fifth switch (15) is with one IGBT for each switch, where each IGBT receives a control signal with a duration equal to the desired duration for the IGBT to conduct. One example of implementation of the second switch (7) is with one thyristor, where the thyristor receives a trigger signal at its appropriate time point as already stated and the thyristor automatically opens when the current flowing through it reaches zero. One example of implementation of the first switch (5) and the third switch (13) is with a thyristor and diode in parallel for each switch, where each thyristor closes at the start of each single-pulse of higher amplitude of biphasic type by receiving a trigger signal and automatically opens at the half-period of the same single-pulse of higher amplitude of biphasic type when the current $I_{L1}$ is zero, allowing the reverse current of the second half-period to flow through the diode. Other implementations may be used, consistent with the spirit of the invention.

Figure 15:
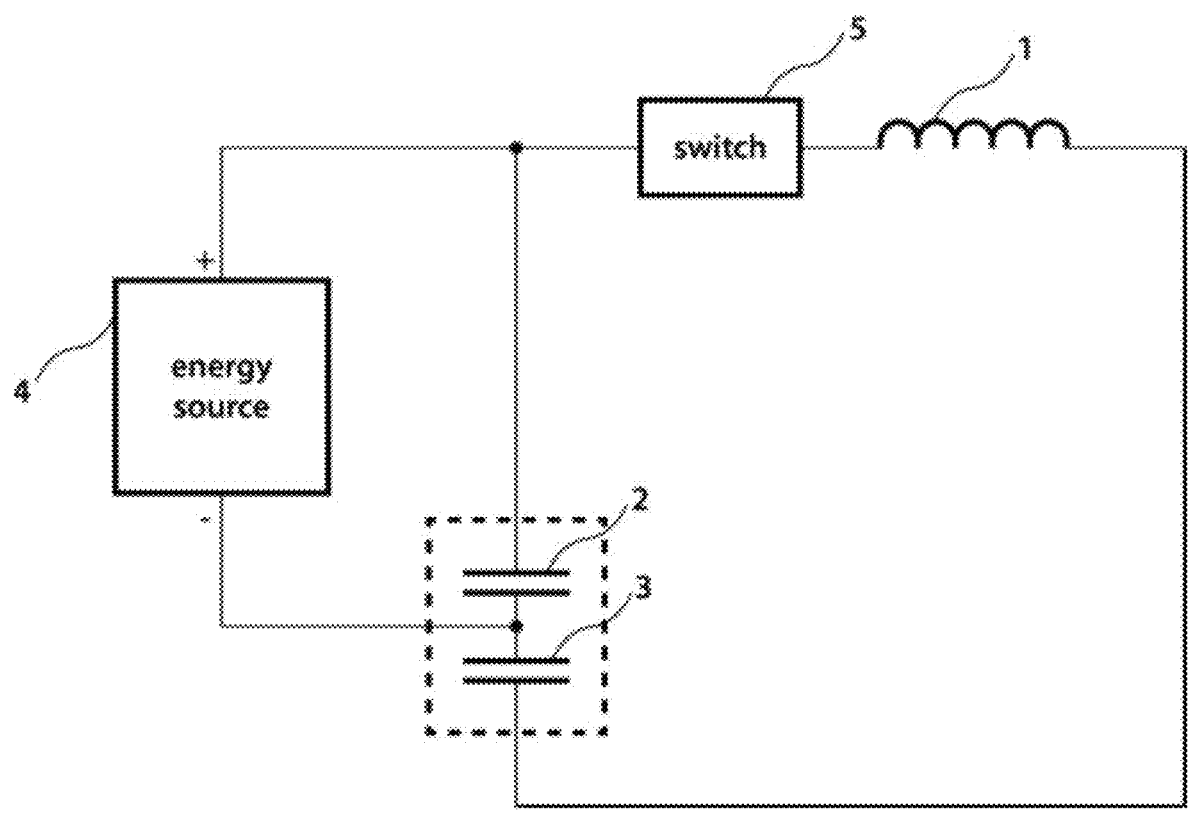
FIG. 15 is an illustrative diagram of a preferred embodiment of a magnetic stimulator with the energy storage devices being disposed within one casing.

Referring to FIG. 15, an illustrative diagram of a preferred embodiment of a magnetic stimulator wherein the two energy storage devices (2) and (3) are disposed within one casing is shown. The embodiment of FIG. 15 is the embodiment of FIG. 1 where the two energy storage devices (2) and (3) are disposed within one casing. The advantages of this implementation is the minimization of the length of the connecting conductors which contributes to decreasing the ohmic resistance of the circuit and thus to reducing the % Voltage Drop, the decrease of the total weight of the magnetic stimulator and the decrease of the manufacturing cost. All other features and the operation of the embodiment of FIG. 15 are the same with the embodiment of FIG. 1. On a similar approach, for any other embodiment of the present invention all energy storage devices comprised in each embodiment can be disposed within one casing.

Figure 16:
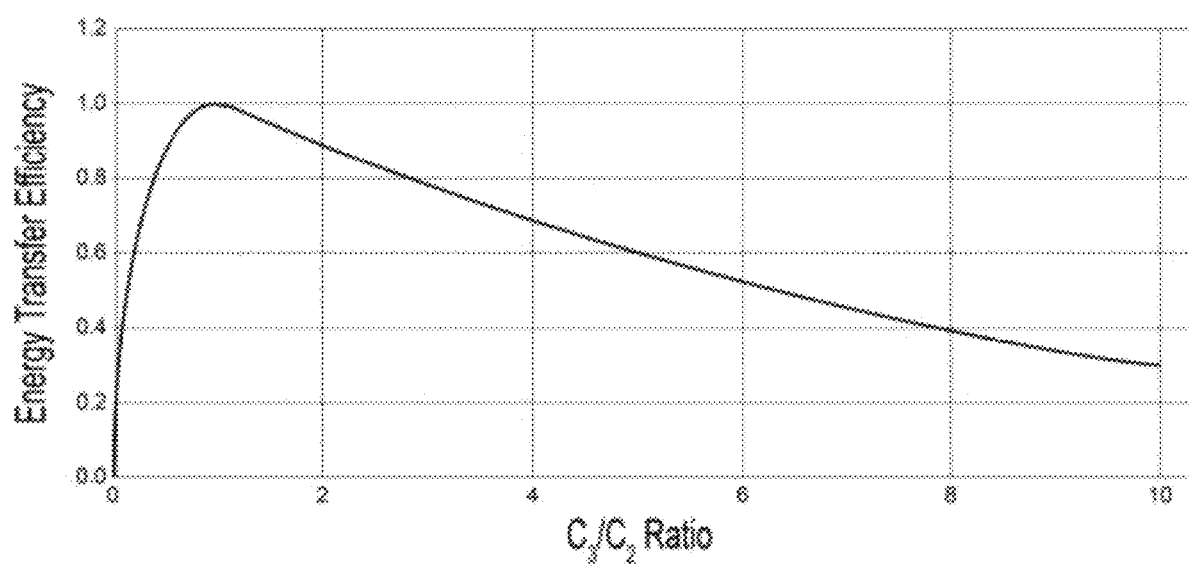
FIG. 16 is an illustrative graph of the relationship between the energy transfer efficiency and the ratio of the capacitances of the two energy storage devices during oscillation of the resonant circuit.

Referring to FIG. 16, an illustrative graph of the relationship between the energy transfer efficiency and the ratio of the capacitances of the two energy storage devices during oscillation of the basic resonant circuit of the invention considering zero ohmic resistance, is shown. Each energy storage device comprises at least one capacitor with the capacitances of the energy storage devices being preferably equal. As disclosed from the graph in FIG. 16, the energy transfer efficiency and the voltage recovery are maximized for a ratio of capacitances where $C_2=C_3$. The ratio of the maximum values of the energies stored in the first energy storage device (2) and in the second energy storage device (3) of the basic resonant circuit during oscillation, considering zero ohmic resistance, is calculated from the equation:

$$\frac{E_{c3,max,t=T/2}}{E_{c2,max,t=0}} = \frac{4C_3}{C_2} \frac{1}{(1+\frac{C_3}{C_2})^2}$$

In the case of any of the two energy storage devices (2) and (3) consisting of more than one capacitor connected in series and/or in parallel, the equivalent total capacitance of the energy storage device consisting of more than one capacitor is computed by the capacitances of the capacitors based on the way they are interconnected, in series or in parallel.

Figure 17:
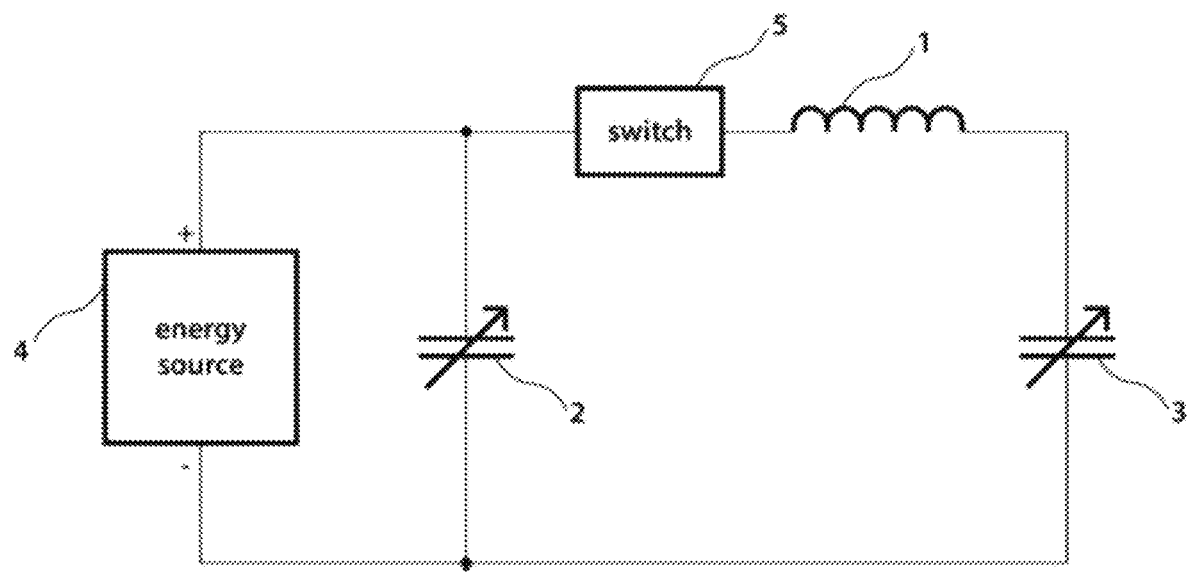
FIG. 17 is an illustrative diagram of an optional embodiment of a magnetic stimulator with independently selectable capacitance of each energy storage device.

Referring to FIG. 17, an illustrative diagram of an optional embodiment of a magnetic stimulator wherein the capacitance of the first energy storage device (2) and the capacitance of the second energy storage device (3) are independently selectable, is shown. One example of implementation of energy storage device with selectable capacitance is a variable capacitor whose capacitance can be changed mechanically or electronically. Another example of implementation of energy storage device with selectable capacitance is a bank of capacitors interconnected together in series and/or in parallel where the total capacitance of the bank can be changed with the operation of switches that either engage or disengage the individual capacitors. A first advantage of the embodiment of FIG. 17 is the possibility to selectively adjust the duration of the current pulses for any type and waveform of current pulse by changing the capacitance of each of the two energy storage devices (2) and (3) and retaining them equal after the change so that the energy transfer efficiency is maximized. The possibility to adjust the duration of the current pulses is a desired feature in magnetic stimulation because different durations invoke different physiological and biological reactions to the tissues. A second advantage of the embodiment of FIG. 17 is the possibility to selectively adjust the voltage transfer ratio between the two energy storage devices (2) and (3) during oscillation in the case the capacitances of the two energy storage devices (2) and (3) are changed and after the change not being equal. The adjustment of the voltage transfer ratio is preferred in cases of desiring the two energy storage devices (2) and (3) to be charged and discharged with different voltage values either lower or higher.

Figure 18:
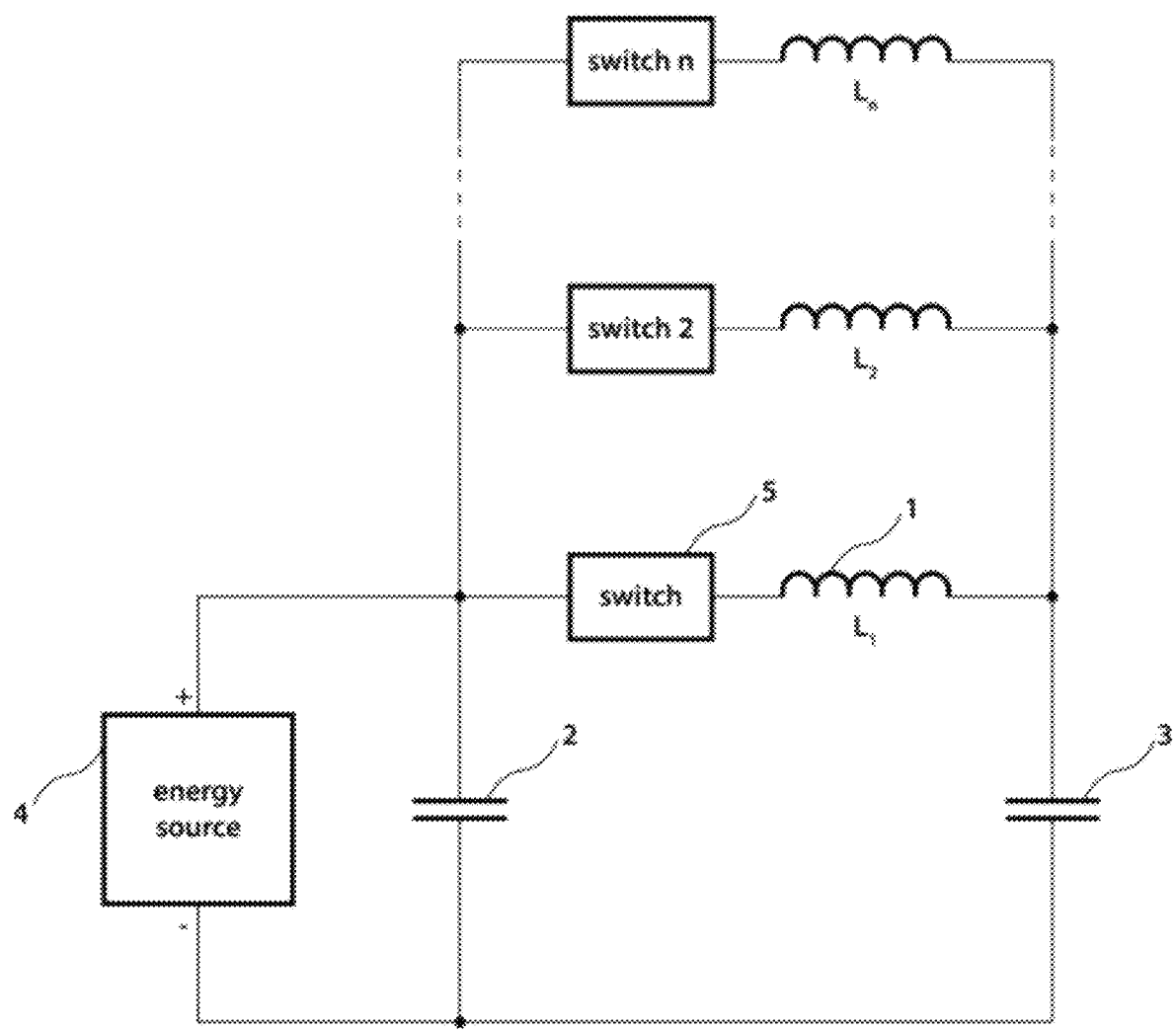
FIG. 18 is an illustrative diagram of an optional embodiment of a magnetic stimulator that is the embodiment of FIG. 1 further comprising (n−1) switches and (n−1) magnetic field generating devices, wherein each switch is connected in series with one magnetic field generating device forming a serial connection and all serial connections are connected in parallel to one another and in parallel to the serial connection of the first switch and the first magnetic field generating device.

Referring to FIG. 18, an illustrative diagram of an optional embodiment of a magnetic stimulator for selectively engaging similar or different, simultaneously or not, magnetic field generating devices in the basic resonant circuit is shown. The embodiment of FIG. 18 is the embodiment of FIG. 1 further comprising a plurality of switches and magnetic field generating devices, wherein each switch is connected in series with one magnetic field generating device forming a serial connection and all serial connections are connected in parallel to one another and in parallel to the serial connection of the first switch and the first magnetic field generating device. More specifically the embodiment of FIG. 18 is the embodiment of FIG. 1 further comprising a plurality of switches (switch 2-switch n) and magnetic field generating devices (magnetic field generating device $L_2$-magnetic field generating device $L_n$), wherein each switch is connected in series with one magnetic field generating device forming a serial connection (switch 2+magnetic field generating device $L_2$, . . . , switch n+magnetic field generating device $L_n$) and all serial connections are connected in parallel to one another and in parallel to the serial connection of the first switch (5) and the first magnetic field generating device (1). The selective operation of the switches allows to engage in different ways the magnetic field generating devices in the basic resonant circuit constituted along with the two energy storage devices (2) and (3). The generated current pulses can be polyphasic or biphasic or half-sine, the choice of which depends on the selected time points of closing and opening each switch. One way of engaging the magnetic field generating devices is simultaneously where the switches connected in series to the selected magnetic field generating devices to be engaged simultaneously, open and close concurrently. As a result the engaged magnetic field generating devices have an equivalent total inductance equal to the sum of inductances connected in parallel and current pulses are generated simultaneously around the engaged magnetic field generating devices. Another way of engaging the magnetic field generating devices is not simultaneously where the switches connected in series to the selected magnetic field generating devices to be engaged open and close at different time points based on the desired type of current pulse to be generated around each selected magnetic field generating device and on a desired order. The magnetic field generating devices can be the same or different in regard to their inductances, shapes, sizes, orientations and focuses. The optional embodiment of FIG. 18 facilitates the application of magnetic stimulation in larger or different areas, in shorter times, with magnetic field generating devices of different shape, size, orientation and focus or with more complex orientations and focuses when simultaneously applying more than one magnetic field generating devices at an area. All switches can be can be implemented with any kind of switching components or their combinations, such as thyristor, diode, IGBT, MOSFET, JFET, BJT. Other switching components may be used, consistent with the spirit of the invention. The possibility of the embodiment of FIG. 18 to generate different types of current pulses is not restricted to the commonly used types but is extended to the generation of any arbitrary waveform of current pulse which can be generated by accordingly adjusting the selected time points of opening and closing each switch.

Figure 19:
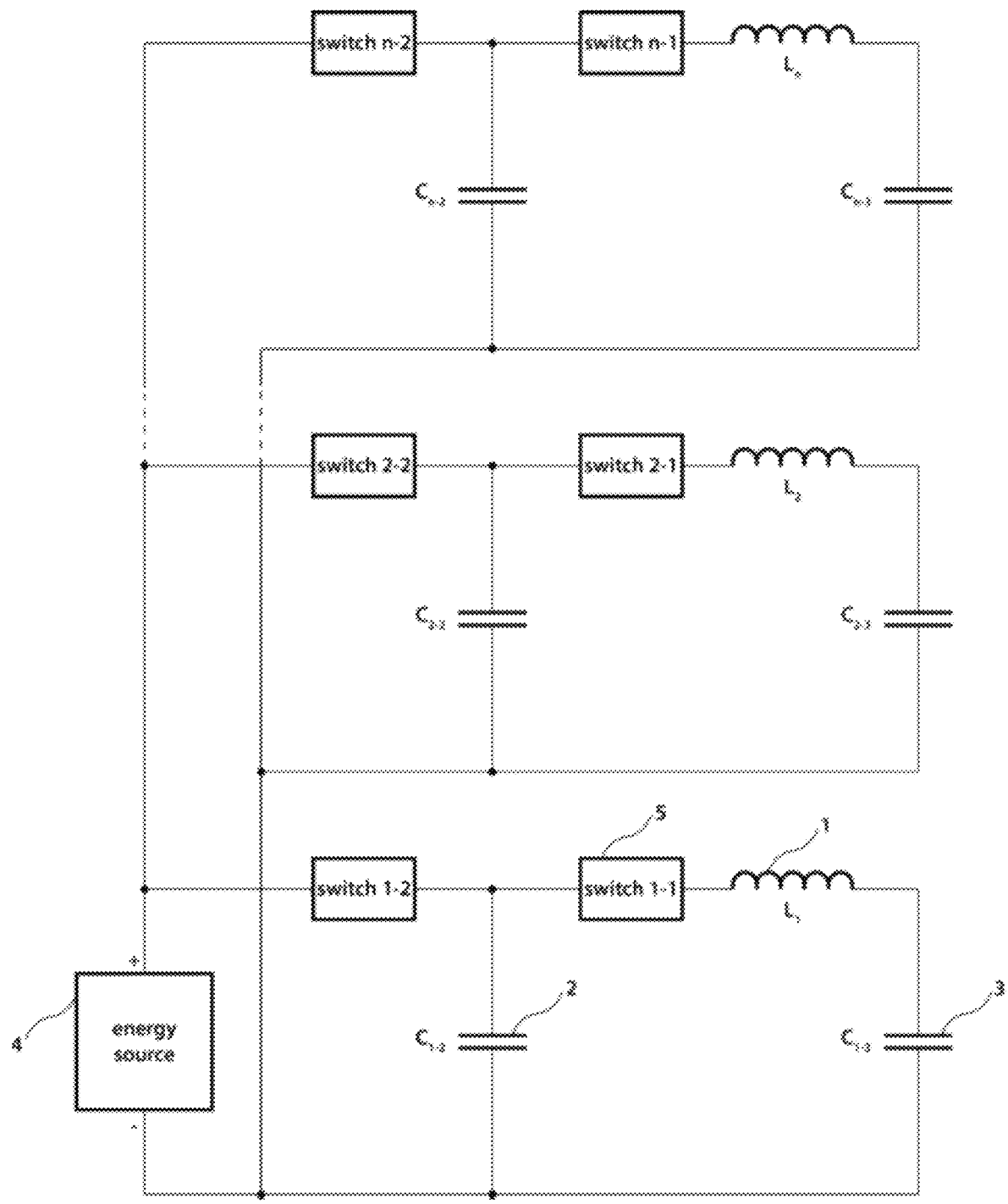
FIG. 19 is an illustrative diagram of an optional embodiment of a magnetic stimulator that is the embodiment of FIG. 1 further comprising (n−1) electrical oscillating resonant circuits each constituted by a connection in series of two energy storage devices, a switch and a magnetic field generating device, wherein one of the two energy storage devices of each electrical oscillating resonant circuit is coupled with a switch to the energy source and to the other electrical oscillating resonant circuits.

Referring to FIG. 19, an illustrative diagram of an optional embodiment of a magnetic stimulator for operating independently a plurality of electrical oscillating resonant circuits, all sharing a common energy source (4) is shown. The embodiment of FIG. 19 is the embodiment of FIG. 1 further comprising a plurality of electrical oscillating resonant circuits each constituted by a connection in series of two energy storage devices, a switch and a magnetic field generating device, wherein each electrical oscillating resonant circuit is coupled to the energy source and the other electrical oscillating resonant circuits with a switch which is configured to selectively disconnect the electrical oscillating resonant circuit from the energy source and the other electrical oscillating resonant circuits. More specifically the embodiment of FIG. 19 is the embodiment of FIG. 1 further comprising a plurality of electrical oscillating resonant circuits each constituted by a connection in series of two energy storage devices, a magnetic field generating device and a switch (energy storage device $C_{2-2}$+switch 2-1+magnetic field generating device $L_2$+energy storage device $C_{2-3}$, . . . , energy storage device $C_{n-2}$+switch n-1+magnetic field generating device $L_n$+energy storage device $C_{n-3}$) wherein each electrical oscillating resonant circuit is coupled to the energy source (4) and the other electrical oscillating resonant circuits with a switch (switch 1-2, switch 2-2, . . . , switch n-2) which is configured to selectively disconnect the electrical oscillating resonant circuit from the energy source (4) and the other electrical oscillating resonant circuits. The switches 1-2, switch 2-2, . . . , switch n-2 allow the selective charging of the respective energy storage devices $C_{1-2}$, $C_{2-2}$, . . . , $C_{n-2}$) and the independent operation of the different electrical oscillating resonant circuits. Each electrical oscillating resonant circuit is similar to the electrical oscillating resonant circuit of the embodiment of FIG. 1 with which share the same features, operation and performance and the possibility of being further extended to implement the optional embodiments deriving from the embodiment of FIG. 1.

Figure 20:
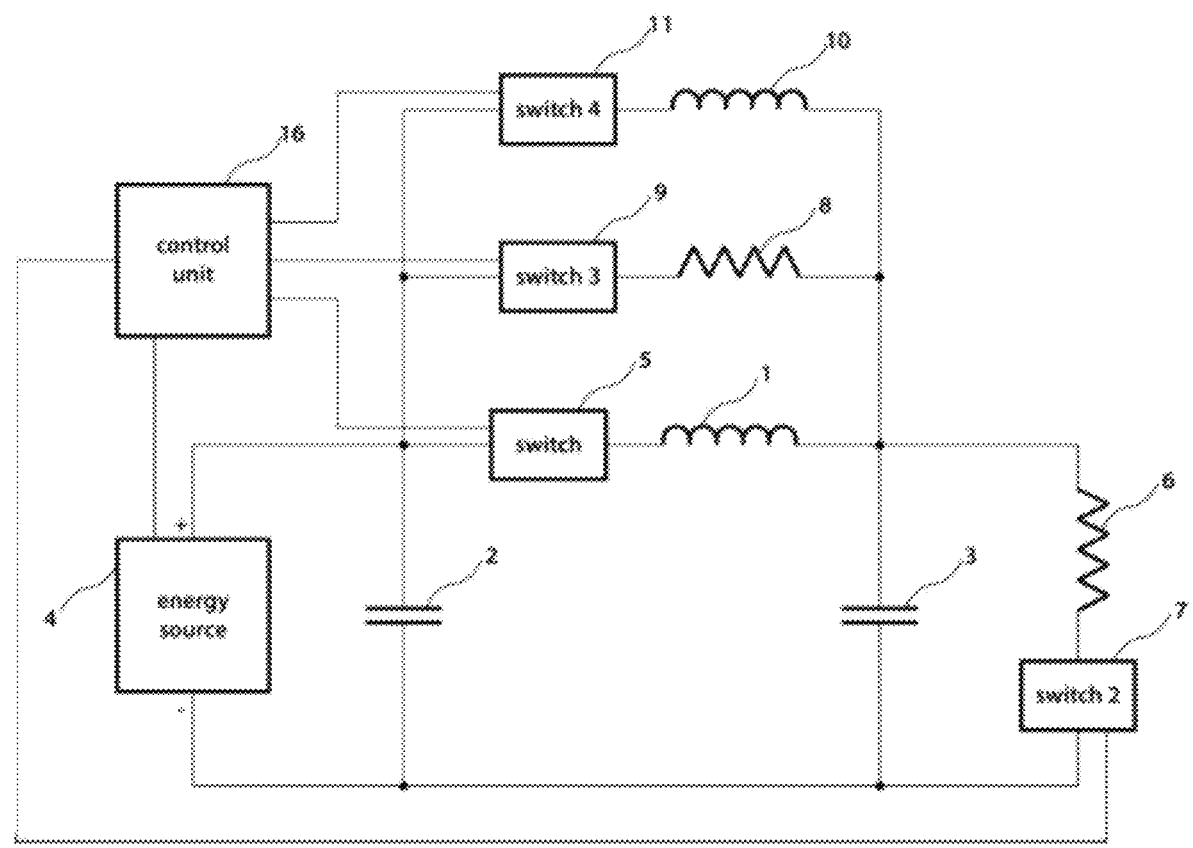
FIG. 20 is an illustrative diagram of an optional embodiment of a magnetic stimulator that is the embodiment of FIG. 11 further comprising a control unit to control the energy source and the switches so to allow the continuous adjustment and the modulation of the output of the energy source, of the amplitude of the current pulses, of the repetition rate of the current pulses and of the type of the current pulses, wherein the current pulses include the current pulses flowing through the magnetic field generating devices.

Referring to FIG. 20, an illustrative diagram of an optional embodiment of a magnetic stimulator further comprising a control unit (16) configured to control the energy source (4) and all the switches to allow the continuous adjustment and the modulation of the output of the energy source, of the amplitude of the current pulses, of the repetition rate of the current pulses and of the type of the current pulses, wherein the current pulses include the current pulses flowing through the two magnetic field generating devices (1) and (10), is shown. The embodiment of FIG. 20 is the embodiment of FIG. 11 further comprising a control unit (16) coupled to the energy source (4), the first switch (5), the second switch (7), the third switch (9), the fourth switch (11) and configured to control their operation. The control unit (16) is implemented to the embodiment of FIG. 11 by way of example as it can be implemented to control the energy source and the switches of any other embodiment of the present invention. The parameters which can be continuously adjusted and modulated are the output of the energy source (4), the amplitude of the current pulses, the repetition rate of the current pulses and the type of the current pulses and the control unit is configured to perform this complex task. The continuous adjustment of the parameters includes the change of their values, by way of example, over a selected continuous range of values and/or over selected discrete values. The modulation of the parameters includes the possibility to define, by way of example, selected durations of zero value of the parameters, selected durations of non-zero values of the parameters, repeatability of the selected durations of zero and non-zero values of the parameters and dynamic change of the values of the parameters and/or the durations of the zero and non-zero values based on different patterns such as, by way of example, ramp-up, ramp-down, trapezoid, sinusoid and combinations of the aforementioned. The continuous adjustment and modulation of the output of the energy source (4) is achieved by the control unit (16) which controls the operation of the energy source (4). The continuous adjustment and modulation of the amplitude of the current pulses, the repetition rate of the current pulses and the type of the current pulses is achieved by the control unit (16) which controls the operation of all the switches (5), (7), (9) and (11).

What is claimed is:

1. A magnetic stimulation device, comprising:
   a first magnetic field generating device, a first energy storage device, and a second energy storage device, wherein all three devices are connected in series to form an electrical oscillating resonant circuit;
   an energy source coupled to the first energy storage device; and
   a first switch to allow charging of the first energy storage device from the energy source and initiating electrical oscillation of the resonant circuit, wherein after the initiation of the electrical oscillation the two energy storage devices repetitively exchange electric charge through the first magnetic field generating device due to the electrical oscillation of the resonant circuit and a time varying magnetic field is generated.

2. Magnetic stimulation device according to claim 1, wherein (a) the first energy storage device and the second energy storage device each comprises terminals and (b) voltage across the terminals of each of the two energy storage devices has always the same polarity.

3. Magnetic stimulation device according to claim 1, wherein no current is flowing through the first magnetic field generating device during charging of the first energy storage device from the energy source.

4. Magnetic stimulation device according to claim 1, wherein the energy source is protected against reverse voltage polarity.

5. Magnetic stimulation device according to claim 1, wherein (i) the magnetic stimulation device comprises one or more additional switches and (ii) after the initiation of the electrical oscillation of the resonant circuit the two energy storage devices repetitively exchange electric charge without an operation of the first switch and the one or more additional switches.

6. Magnetic stimulation device according to claim 1, wherein the first switch opens and closes at selectable time points in order to halt the electrical oscillation of the resonant circuit.

7. Magnetic stimulation device according to claim 1, wherein a position of the first switch is adapted to allow charging of the second energy storage device from the energy source and initiating electrical oscillation of the resonant circuit.

8. Magnetic stimulation device according to claim 6, further comprising a serial connection of a first resistor and a second switch and the serial connection of the first resistor and the second switch is connected in parallel to the second energy storage device to selectively discharge either one of the two or both the energy storage devices.

9. Magnetic stimulation device according to claim 8, further comprising a serial connection of a third switch and a second resistor and the serial connection of the third switch and the second resistor is connected in parallel to the serial connection of the first switch and the first magnetic field generating device.

10. Magnetic stimulation device according to claim 8, further comprising a serial connection of a third switch and a second magnetic field generating device and the serial connection of the third switch and the second magnetic field generating device is connected in parallel to the serial connection of the first switch and the first magnetic field generating device.

11. Magnetic stimulation device according to claim 8, further comprising a serial connection of a third switch and a second resistor and a serial connection of a fourth switch and a second magnetic field generating device, wherein the serial connection of the third switch and the second resistor and the serial connection of the fourth switch and the second magnetic field generating device are connected in parallel to the serial connection of the first switch and the first magnetic field generating device.

12. Magnetic stimulation device according to claim 8, further comprising:
   a serial connection of a third energy storage device and a third switch and the serial connection of the third energy storage device and the third switch is connected in parallel to the serial connection of the first magnetic field generating device and the second energy storage device, wherein the third energy storage device is further coupled to the energy source; and
   a fourth and a fifth switch to allow the energy source to selectively charge either only the first energy storage device or only the third energy storage device or both.

13. Magnetic stimulation device according to claim 1, wherein the energy storage devices are disposed within one casing.

14. Magnetic stimulation device according to claim 1, wherein each energy storage device comprises at least one capacitor with capacitances of the energy storage devices being equal.

15. Magnetic stimulation device according to claim 1, wherein capacitance of each energy storage device is independently selectable.

16. Magnetic stimulation device according to claim 1, further comprising a plurality of switches and magnetic field generating devices, wherein each switch is connected in series with one magnetic field generating device forming a serial connection and all serial connections are connected in parallel to one another and in parallel to the serial connection of the first switch and the first magnetic field generating device.

17. Magnetic stimulation device according to claim 1, further comprising a plurality of electrical oscillating resonant circuits each constituted by a connection in series of two energy storage devices, a switch and a magnetic field generating device, wherein one of the two energy storage devices of each electrical oscillating resonant circuit is coupled with a switch to the energy source and to the other electrical oscillating resonant circuits.

18. Magnetic stimulation device according to claim 11, further comprising a control unit to control the energy source and the switches so to allow continuous adjustment and modulation of output of the energy source, of amplitude of current pulses, of repetition rate of current pulses and of type of current pulses, wherein the current pulses include current pulses flowing through the magnetic field generating devices.

* * * * *